(12) United States Patent
Montminy

(10) Patent No.: US 6,646,115 B1
(45) Date of Patent: Nov. 11, 2003

(54) IDENTIFICATION OF TRANSCRIPTION FACTOR WITHIN A CAMP-RESPONSIVE TRANSCRIPTIONAL ENHANCER BINDING PROTEIN (CREB), AND USES THEREFORE

(75) Inventor: Marc R. Montminy, Wellesley, MA (US)

(73) Assignee: The Salk Institute for Biological Studies, La Jolla, CA (US)

( * ) Notice: Subject to any disclaimer, the term of this patent is extended or adjusted under 35 U.S.C. 154(b) by 19 days.

(21) Appl. No.: 09/686,316

(22) Filed: Oct. 10, 2000

Related U.S. Application Data

(60) Division of application No. 09/515,276, filed on Feb. 29, 2000, which is a continuation-in-part of application No. 08/961,739, filed on Oct. 31, 1997, now Pat. No. 6,063,583, which is a continuation-in-part of application No. 08/194,468, filed on Feb. 10, 1994, now Pat. No. 5,750,336.

(51) Int. Cl.[7] .......................... C07H 21/04; C12Q 1/68
(52) U.S. Cl. ........................................ 536/23.5; 435/6
(58) Field of Search .............................. 536/23.5; 435/6

(56) References Cited

U.S. PATENT DOCUMENTS

| | | | | |
|---|---|---|---|---|
| 5,582,995 A | * | 12/1996 | Avruch et al. | 435/71 |
| 5,705,342 A | * | 1/1998 | Bischoff et al. | 435/6 |
| 5,750,336 A | * | 5/1998 | Montminy | 435/6 |

FOREIGN PATENT DOCUMENTS

| | | | |
|---|---|---|---|
| WO | WO 90/05745 | * | 5/1990 |

OTHER PUBLICATIONS

Sheng et al., CREB: A Ca2+–Regulated Transcription Factor Phosphorylated by Calmodulin–Dependent Kinases. Science 252:1427–1430, 1991.*
Alberts et al., "Protein Phosphatase 2A Potentiates Activity of Promoters Containing AP–1–Binding Elements" in *Mol. and Cell Biol.* 13:2104–2112 (1993).
Boyle et al., "Activation of Protein Kinase C Decreases Phosphorylation of c–Jun at Sites That Negatively Regulate Its DNA–Binding Activity" in *Cell* 64:573–584 (1991).
Chrivia et al., "Phosphorylated CREB binds specifically to the nuclear protein CBP" in *Nature* 365:855–859 (1993).
Gonzalez et al., "Characterization of Motifs Which Are Critical for Activity of the Cyclic AMP–Responsive Transcription Factor CREB" in *Mol. and Cell Biol.* 11(3):1306–1312 (1991).
Hagiwara et al., "Transcriptional Attenuation Following cAMP Induction Requires PP–1–Mediated Dephosphorylation of CREB" *Cell* 70:105–113 (1992).
Hibi et al., "Identification of an oncoprotein–and UV–responsive protein kinase that binds and potentiates the c–Jun activation domain" in *Genes and Develop.* 7:2135–2148 (1993).

Hill et al., "Functional Analysis of a Growth Factor–Responsive Transcription Factor Complex" in *Cell* 73:395–406 (1993).
Hollenberg and Evans, "Multiple and Cooperative TransActivation Domains of the Human Glucocorticoid Receptor" in *Cell* 55:899–906 (1988).
Keegan et al., "Separation of DNA Binding from the Transcription–Activating Function of a Eukaryotic Regulatory Protein" *Science* 231:699–704 (1986).
Leonard et al., "Characterization of Somatostatin Transactvating Factor–1, a Novel Homeobox Factor That Stimulates Somatostatin Expression in Pancreatic Islet Cells" in Mol. Endocr. 7:1275–1283 (1993).
Nakajima et al., "Analysis of a cAMP–responsive activator reveals a two–component mechanism for transcriptional induction via signal–dependent factors" Genes Dev (1997) 11(6):738–747.
Parker et al., "Phosphorylation of CREB at Ser–133 Induces Complex Formation with CREB–Binding Protein via a Direct Mechanism" Mol Cell Biol (1996) 16(2):694–703.
Smeal et al., "Oncogenic and transcriptional cooperation with Ha–Ras requires phosphorylation of c–Jun on serines 63 and 73" in *Nature* 354:494–496 (1991).
Webster et al., "The Hormone–Binding Domains of the Estrogen and Glucocorticoid Receptors Contain an Inducible Transcription Activation Function" in *Cell* 54:199–207 (1988).
Webster et al., "The Yeast $UAS_G$ Is a Transcriptional Enhancer in Human HeLa Cells in the Presence of the GAL4 Trans–Activator" in Cell 52:169–178 (1988).
Montminy et al., Regulation of somatostatin gene transcription by cyclic adenosine monophosphate, Metabolism 45 (8 Suppl 1):4–7, Aug. 1996.*

* cited by examiner

*Primary Examiner*—Donna Wortman
(74) *Attorney, Agent, or Firm*—Foley & Lardner; Stephen E. Reiter

(57) ABSTRACT

In accordance with the present invention, it has been discovered that CREB binding protein (CBP) cooperates with upstream activators involved in the activation of transcription of such signal dependent transcription factors as c-Jun (responsive to phorbol ester), serum response factor, and the like. It has also been discovered that CBP can be employed in an assay to identify compounds which disrupt the ability of such signal dependent transcription factors to activate transcription. In another aspect, it has been discovered that CBP can be employed in an assay to identify new signal dependent transcription factors. In yet another aspect of the present invention, it has been discovered that CBP can be employed in an assay to identify novel co-factor protein(s) which mediate the interaction between signal dependent transcription factors and inducer molecules involved in the activation of transcription. Accordingly, the present invention provides methods for the identification of compounds which inhibit activation of cAMP and mitogen responsive genes and methods for the identification of novel signal dependent transcription factors and co-factor proteins. In still another aspect, methods employing compounds which inhibit intracellular signal-induced response pathways have been developed for the treatment of diabetes mellitus.

3 Claims, 2 Drawing Sheets

SEQUENCE LISTING

<160> NUMBER OF SEQ ID NOS: 4

<210> SEQ ID NO 1
<211> LENGTH: 7326
<212> TYPE: DNA
<213> ORGANISM: Mus

-continued

```
<220> FEATURE:
<221> NAME/KEY: CDS
<222> LOCATION: (1)...(7326)
<220> FEATURE:
<221> NAME/KEY: misc_feature
<222> LOCATION: (1)...(7326)
<223> OTHER INFORMATION: n = A,T,C or G

<400> SEQUENCE: 1 atg gcc gag aac ttg ctg gac gga ccg ccc aac ccc aaa cga gcc aaa      48
Met Ala Glu Asn Leu Leu Asp Gly Pro Pro Asn Pro Lys Arg Ala Lys
  1               5                  10                  15 ctc agc tcg ccc ggc ttc tcc gcg aat gac aac aca gat ttt gga tca      96
Leu Ser Ser Pro Gly Phe Ser Ala Asn Asp Asn Thr Asp Phe Gly Ser
             20                  25                  30 ttg ttt gac ttg gaa aat gac ctt cct gat gag ctg atc ccc aat gga     144
Leu Phe Asp Leu Glu Asn Asp Leu Pro Asp Glu Leu Ile Pro Asn Gly
         35                  40                  45 gaa tta agc ctt tta aac agt ggg aac ctt gtt cca gat gct gcg tcc     192
Glu Leu Ser Leu Leu Asn Ser Gly Asn Leu Val Pro Asp Ala Ala Ser
     50                  55                  60 aaa cat aaa caa ctg tca gag ctt ctt aga gga ggc agc ggc tct agc     240
Lys His Lys Gln Leu Ser Glu Leu Leu Arg Gly Gly Ser Gly Ser Ser
 65                  70                  75                  80 atc aac cca ggg ata ggc aat gtg agt gcc agc agc cct gtg caa cag     288
Ile Asn Pro Gly Ile Gly Asn Val Ser Ala Ser Ser Pro Val Gln Gln
                 85                  90                  95 ggc ctt ggt ggc cag gct cag ggg cag ccg aac agt aca aac atg gcc     336
Gly Leu Gly Gly Gln Ala Gln Gly Gln Pro Asn Ser Thr Asn Met Ala
            100                 105                 110 agc tta ggt gcc atg ggc aag agc cct ctg aac caa gga gac tca tca     384
Ser Leu Gly Ala Met Gly Lys Ser Pro Leu Asn Gln Gly Asp Ser Ser
        115                 120                 125 aca ccc aac ctg ccc aaa cag gca gcc agc acc tct ggg ccc act ccc     432
Thr Pro Asn Leu Pro Lys Gln Ala Ala Ser Thr Ser Gly Pro Thr Pro
    130                 135                 140 cct gcc tcc caa gca ctg aat cca caa gca caa aag caa gta ggg ctg     480
Pro Ala Ser Gln Ala Leu Asn Pro Gln Ala Gln Lys Gln Val Gly Leu
145                 150                 155                 160 gtg acc agt agt cct gcc aca tca cag act gga cct ggg atc tgc atg     528
Val Thr Ser Ser Pro Ala Thr Ser Gln Thr Gly Pro Gly Ile Cys Met
                165                 170                 175 aat gct aac ttc aac cag acc cac cca ggc ctt ctc aat agt aac tct     576
Asn Ala Asn Phe Asn Gln Thr His Pro Gly Leu Leu Asn Ser Asn Ser
            180                 185                 190 ggc cat agc tta atg aat cag gct caa caa ggg caa gct caa gtc atg     624
Gly His Ser Leu Met Asn Gln Ala Gln Gln Gly Gln Ala Gln Val Met
        195                 200                 205 aat gga tct ctt ggg gct gct gga aga gga agg gga gct gga atg ccc     672
Asn Gly Ser Leu Gly Ala Ala Gly Arg Gly Arg Gly Ala Gly Met Pro
    210                 215                 220 tac cct gct cca gcc atg cag ggg gcc aca agc agt gtg ctg gcg gag     720
Tyr Pro Ala Pro Ala Met Gln Gly Ala Thr Ser Ser Val Leu Ala Glu
225                 230                 235                 240 acc ttg aca cag gtt tcc cca caa atg gct ggc cat gct gga cta aat     768
Thr Leu Thr Gln Val Ser Pro Gln Met Ala Gly His Ala Gly Leu Asn
                245                 250                 255 aca gca cag gca gga ggc atg acc aag atg gga atg act ggt acc aca     816
Thr Ala Gln Ala Gly Gly Met Thr Lys Met Gly Met Thr Gly Thr Thr
            260                 265                 270 agt cca ttt gga caa ccc ttt agt caa act gga ggg cag cag atg gga     864
```

-continued

```
Ser Pro Phe Gly Gln Pro Phe Ser Gln Thr Gly Gly Gln Gln Met Gly
            275                 280                 285 gcc act gga gtg aac ccc cag tta gcc agc aaa cag agc atg gtc aat      912
Ala Thr Gly Val Asn Pro Gln Leu Ala Ser Lys Gln Ser Met Val Asn
        290                 295                 300 agt tta cct gct ttt cct aca gat atc aag aat act tca gtc acc act      960
Ser Leu Pro Ala Phe Pro Thr Asp Ile Lys Asn Thr Ser Val Thr Thr
305                 310                 315                 320 gtg cca aat atg tcc cag ttg caa aca tca gtg gga att gta ccc aca     1008
Val Pro Asn Met Ser Gln Leu Gln Thr Ser Val Gly Ile Val Pro Thr
                325                 330                 335 caa gca att gca aca ggc ccc aca gca gac cct gaa aaa cgc aaa ctg     1056
Gln Ala Ile Ala Thr Gly Pro Thr Ala Asp Pro Glu Lys Arg Lys Leu
            340                 345                 350 ata cag cag cag ctg gtt cta ctg ctt cat gcc cac aaa tgt cag aga     1104
Ile Gln Gln Gln Leu Val Leu Leu Leu His Ala His Lys Cys Gln Arg
        355                 360                 365 cga gag caa gca aat gga gag gtt cgn gcc tgt tct ctc cca cac tgt     1152
Arg Glu Gln Ala Asn Gly Glu Val Xaa Ala Cys Ser Leu Pro His Cys
370                 375                 380 cga acc atg aaa aac gtt ttg aat cac atg aca cat tgt cag gct ccc     1200
Arg Thr Met Lys Asn Val Leu Asn His Met Thr His Cys Gln Ala Pro
385                 390                 395                 400 aaa gcc tgc caa gtt gcc cat tgt gca tct tca cga caa atc atc tct     1248
Lys Ala Cys Gln Val Ala His Cys Ala Ser Ser Arg Gln Ile Ile Ser
                405                 410                 415 cat tgg aag aac tgc aca cga cat gac tgt cct gtt tgc ctc cct ttg     1296
His Trp Lys Asn Cys Thr Arg His Asp Cys Pro Val Cys Leu Pro Leu
            420                 425                 430 aaa aat gcc agt gac aag cga aac caa caa acc atc ctg gga tct cca     1344
Lys Asn Ala Ser Asp Lys Arg Asn Gln Gln Thr Ile Leu Gly Ser Pro
        435                 440                 445 gct agt gga att caa aac aca att ggt tct gtt ggt gca ggg caa cag     1392
Ala Ser Gly Ile Gln Asn Thr Ile Gly Ser Val Gly Ala Gly Gln Gln
450                 455                 460 aat gcc act tcc tta agt aac cca aat ccc ata gac ccc agt tcc atg     1440
Asn Ala Thr Ser Leu Ser Asn Pro Asn Pro Ile Asp Pro Ser Ser Met
465                 470                 475                 480 cag cgg gcc tat gct gct cta gga ctc ccc tac atg aac cag cct cag     1488
Gln Arg Ala Tyr Ala Ala Leu Gly Leu Pro Tyr Met Asn Gln Pro Gln
                485                 490                 495 acg cag ctg cag cct cag gtt cct ggc cag caa cca gca cag cct cca     1536
Thr Gln Leu Gln Pro Gln Val Pro Gly Gln Gln Pro Ala Gln Pro Pro
            500                 505                 510 gcc cac cag cag atg agg act ctc aat gcc cta gga aac aac ccc atg     1584
Ala His Gln Gln Met Arg Thr Leu Asn Ala Leu Gly Asn Asn Pro Met
        515                 520                 525 agt gtc cca gca gga gga ata aca aca gat caa cag cca cca aac ttg     1632
Ser Val Pro Ala Gly Gly Ile Thr Thr Asp Gln Gln Pro Pro Asn Leu
530                 535                 540 att tca gaa tca gct ctt cca act tcc ttg ggg gct acc aat cca ctg     1680
Ile Ser Glu Ser Ala Leu Pro Thr Ser Leu Gly Ala Thr Asn Pro Leu
545                 550                 555                 560 atg aat gat ggt tca aac tct ggt aac att gga agc ctc agc acg ata     1728
Met Asn Asp Gly Ser Asn Ser Gly Asn Ile Gly Ser Leu Ser Thr Ile
                565                 570                 575 cct aca gca gcg cct cct tcc agc act ggt gtt cga aaa ggc tgg cat     1776
Pro Thr Ala Ala Pro Pro Ser Ser Thr Gly Val Arg Lys Gly Trp His
            580                 585                 590
```

```
                                    -continued gaa cat gtg act cag gac cta cgg agt cat cta gtc cat aaa ctc gtt    1824
Glu His Val Thr Gln Asp Leu Arg Ser His Leu Val His Lys Leu Val
        595                 600                 605 caa gcc atc ttc cca act cca gac cct gca gct ctg aaa gat cgc cgc    1872
Gln Ala Ile Phe Pro Thr Pro Asp Pro Ala Ala Leu Lys Asp Arg Arg
    610                 615                 620 atg gag aac ctg gtt gcc tat gct aag aaa gtg gag gga gac atg tat    1920
Met Glu Asn Leu Val Ala Tyr Ala Lys Lys Val Glu Gly Asp Met Tyr
625                 630                 635                 640 gag tct gct aat agc agg gat gaa tac tat cat tta tta gca gag aaa    1968
Glu Ser Ala Asn Ser Arg Asp Glu Tyr Tyr His Leu Leu Ala Glu Lys
                645                 650                 655 atc tat aaa ata caa aaa gaa cta gaa gaa aag cgg agg aca cgt tta    2016
Ile Tyr Lys Ile Gln Lys Glu Leu Glu Glu Lys Arg Arg Thr Arg Leu
            660                 665                 670 cat aag caa ggc atc ctg ggt aac cag cca gct tta cca gct tct ggg    2064
His Lys Gln Gly Ile Leu Gly Asn Gln Pro Ala Leu Pro Ala Ser Gly
        675                 680                 685 gct cag ccc cct gtg att cca cca gcc cag tct gta aga cct cca aat    2112
Ala Gln Pro Pro Val Ile Pro Pro Ala Gln Ser Val Arg Pro Pro Asn
    690                 695                 700 ggg ccc ctg cct ttg cca gtg aat cgc atg cag gtt tct caa ggg atg    2160
Gly Pro Leu Pro Leu Pro Val Asn Arg Met Gln Val Ser Gln Gly Met
705                 710                 715                 720 aat tca ttt aac cca atg tcc ctg gga aac gtc cag ttg cca cag gca    2208
Asn Ser Phe Asn Pro Met Ser Leu Gly Asn Val Gln Leu Pro Gln Ala
                725                 730                 735 ccc atg gga cct cgt gca gcc tcc cct atg aac cac tct gtg cag atg    2256
Pro Met Gly Pro Arg Ala Ala Ser Pro Met Asn His Ser Val Gln Met
            740                 745                 750 aac agc atg gcc tca gtt ccg ggt atg gcc att tct cct tca cgg atg    2304
Asn Ser Met Ala Ser Val Pro Gly Met Ala Ile Ser Pro Ser Arg Met
        755                 760                 765 cct cag cct cca aat atg atg ggc act cat gcc aac aac att atg gcc    2352
Pro Gln Pro Pro Asn Met Met Gly Thr His Ala Asn Asn Ile Met Ala
    770                 775                 780 cag gca cct act cag aac cag ttt ctg cca cag aac cag ttt cca tca    2400
Gln Ala Pro Thr Gln Asn Gln Phe Leu Pro Gln Asn Gln Phe Pro Ser
785                 790                 795                 800 tcc agt ggg gca atg agt gtg aac agt gtg ggc atg ggg caa cca gca    2448
Ser Ser Gly Ala Met Ser Val Asn Ser Val Gly Met Gly Gln Pro Ala
                805                 810                 815 gcc cag gca ggt gtt tca cag ggt cag gaa cct gga gct gct ctc cct    2496
Ala Gln Ala Gly Val Ser Gln Gly Gln Glu Pro Gly Ala Ala Leu Pro
            820                 825                 830 aac cct ctg aac atg ctg gca ccc cag gcc agc cag ctg cct tgc cca    2544
Asn Pro Leu Asn Met Leu Ala Pro Gln Ala Ser Gln Leu Pro Cys Pro
        835                 840                 845 cca gtg aca cag tca cca ttg cac ccg act cca cct cct gct tcc aca    2592
Pro Val Thr Gln Ser Pro Leu His Pro Thr Pro Pro Pro Ala Ser Thr
    850                 855                 860 gct gct ggc atg ccc tct ctc caa cat cca acg gca cca gga atg acc    2640
Ala Ala Gly Met Pro Ser Leu Gln His Pro Thr Ala Pro Gly Met Thr
865                 870                 875                 880 cct cct cag cca gca gct ccc act cag cca tct act cct gtg tca tct    2688
Pro Pro Gln Pro Ala Ala Pro Thr Gln Pro Ser Thr Pro Val Ser Ser
                885                 890                 895 ggg cag act cct acc cca act cct ggc tca gtg ccc agc gct gcc caa    2736
Gly Gln Thr Pro Thr Pro Thr Pro Gly Ser Val Pro Ser Ala Ala Gln
            900                 905                 910
```

```
aca cag agt acc cct aca gtc cag gca gca gca cag gct cag gtg act      2784
Thr Gln Ser Thr Pro Thr Val Gln Ala Ala Ala Gln Ala Gln Val Thr
            915                 920                 925 cca cag cct cag acc cca gtg cag cca cca tct gtg gct act cct cag      2832
Pro Gln Pro Gln Thr Pro Val Gln Pro Pro Ser Val Ala Thr Pro Gln
    930                 935                 940 tca tca cag cag caa cca acg cct gtg cat act cag cca cct ggc aca      2880
Ser Ser Gln Gln Gln Pro Thr Pro Val His Thr Gln Pro Pro Gly Thr
945                 950                 955                 960 ccg ctt tct cag gca gca gcc agc att gat aat aga gtc cct act ccc      2928
Pro Leu Ser Gln Ala Ala Ala Ser Ile Asp Asn Arg Val Pro Thr Pro
                965                 970                 975 tcc act gtg acc agt gct gaa acc agt tcc cag cag cca gga ccc gat      2976
Ser Thr Val Thr Ser Ala Glu Thr Ser Ser Gln Gln Pro Gly Pro Asp
            980                 985                 990 gtg ccc atg ctg gaa atg aag aca gag gtg cag aca gat gat gct gag      3024
Val Pro Met Leu Glu Met Lys Thr Glu Val Gln Thr Asp Asp Ala Glu
        995                 1000                1005 cct gaa cct act gaa tcc aag ggg gaa cct cgg tct gag atg atg gaa      3072
Pro Glu Pro Thr Glu Ser Lys Gly Glu Pro Arg Ser Glu Met Met Glu
    1010                1015                1020 gag gat tta caa ggt tct tcc caa gta aaa gaa gag aca gat acg aca      3120
Glu Asp Leu Gln Gly Ser Ser Gln Val Lys Glu Glu Thr Asp Thr Thr
1025                1030                1035                1040 gag cag aag tca gag cca atg gaa gta gaa gaa aag aaa cct gaa gta      3168
Glu Gln Lys Ser Glu Pro Met Glu Val Glu Glu Lys Lys Pro Glu Val
                1045                1050                1055 aaa gtg gaa gct aaa gag gaa gaa gag aac agt tcg aac gac aca gcc      3216
Lys Val Glu Ala Lys Glu Glu Glu Asn Ser Ser Asn Asp Thr Ala
            1060                1065                1070 tca caa tca aca tct cct tcc cag cca cgc aaa aaa atc ttt aaa ccc      3264
Ser Gln Ser Thr Ser Pro Ser Gln Pro Arg Lys Lys Ile Phe Lys Pro
        1075                1080                1085 gag gag cta cgc cag gca ctt atg cca act cta gaa gca ctc tat cga      3312
Glu Glu Leu Arg Gln Ala Leu Met Pro Thr Leu Glu Ala Leu Tyr Arg
    1090                1095                1100 cag gac cca gag tct ttg cct ttt cgt cag cct gta gat cct cag ctc      3360
Gln Asp Pro Glu Ser Leu Pro Phe Arg Gln Pro Val Asp Pro Gln Leu
1105                1110                1115                1120 cta gga atc cca gat tat ttt gat ata gtg aag aat cct atg gac ctt      3408
Leu Gly Ile Pro Asp Tyr Phe Asp Ile Val Lys Asn Pro Met Asp Leu
                1125                1130                1135 tct acc atc aaa cga aag ctg gac aca ggg caa tat caa gaa ccc tgg      3456
Ser Thr Ile Lys Arg Lys Leu Asp Thr Gly Gln Tyr Gln Glu Pro Trp
            1140                1145                1150 cag tat gtg gat gat gtc agg ctt atg ttc aac aat gcg tgg cta tat      3504
Gln Tyr Val Asp Asp Val Arg Leu Met Phe Asn Asn Ala Trp Leu Tyr
        1155                1160                1165 aat cgt aaa acg tcc cgt gta tat aaa ttt tgc agt aaa ctt gca gag      3552
Asn Arg Lys Thr Ser Arg Val Tyr Lys Phe Cys Ser Lys Leu Ala Glu
    1170                1175                1180 gtc ttt gaa caa gaa att gac cct gtc atg cag tct ctt gga tat tgc      3600
Val Phe Glu Gln Glu Ile Asp Pro Val Met Gln Ser Leu Gly Tyr Cys
1185                1190                1195                1200 tgt gga cga aag tat gag ttc tcc cca cag act ttg tgc tgt tac gga      3648
Cys Gly Arg Lys Tyr Glu Phe Ser Pro Gln Thr Leu Cys Cys Tyr Gly
                1205                1210                1215 aag cag ctg tgt aca att cct cgt gat gca gcc tac tac agc tat cag      3696
Lys Gln Leu Cys Thr Ile Pro Arg Asp Ala Ala Tyr Tyr Ser Tyr Gln
```

-continued

```
             1220                1225                1230
aat agg tat cat ttc tgt ggg aag tgt ttc aca gag atc cag ggc gag    3744
Asn Arg Tyr His Phe Cys Gly Lys Cys Phe Thr Glu Ile Gln Gly Glu
        1235                1240                1245 aat gtg acc ctg ggt gac gac cct tcc caa cct cag acg aca att tcc    3792
Asn Val Thr Leu Gly Asp Asp Pro Ser Gln Pro Gln Thr Thr Ile Ser
    1250                1255                1260 aag gat caa ttt gaa aag aag aaa aat gat acc tta gat cct gaa cct    3840
Lys Asp Gln Phe Glu Lys Lys Lys Asn Asp Thr Leu Asp Pro Glu Pro
1265                1270                1275                1280 ttt gtt gac tgc aaa gag tgt ggc cgg aag atg cat cag att tgt gtt    3888
Phe Val Asp Cys Lys Glu Cys Gly Arg Lys Met His Gln Ile Cys Val
            1285                1290                1295 cta cac tat gac atc att tgg cct tca ggt ttt gtg tgt gac aac tgt    3936
Leu His Tyr Asp Ile Ile Trp Pro Ser Gly Phe Val Cys Asp Asn Cys
        1300                1305                1310 ttg aag aaa act ggc aga cct cgg aaa gaa aac aaa ttc agt gct aag    3984
Leu Lys Lys Thr Gly Arg Pro Arg Lys Glu Asn Lys Phe Ser Ala Lys
    1315                1320                1325 agg ctg cag acc aca cga ttg gga aac cac tta gaa gac aga gtg aat    4032
Arg Leu Gln Thr Thr Arg Leu Gly Asn His Leu Glu Asp Arg Val Asn
1330                1335                1340 aag ttt ttg cgg cgc cag aat cac cct gaa gct ggg gag gtt ttt gtc    4080
Lys Phe Leu Arg Arg Gln Asn His Pro Glu Ala Gly Glu Val Phe Val
1345                1350                1355                1360 aga gtg gtg gcc agc tca gac aag act gtg gag gtc aag ccg gga atg    4128
Arg Val Val Ala Ser Ser Asp Lys Thr Val Glu Val Lys Pro Gly Met
            1365                1370                1375 aag tca agg ttt gtg gat tct gga gag atg tcg gaa tct ttc cca tat    4176
Lys Ser Arg Phe Val Asp Ser Gly Glu Met Ser Glu Ser Phe Pro Tyr
        1380                1385                1390 cgt acc aaa gca ctc ttt gct ttt gag gag atc gat gga gtc gat gtg    4224
Arg Thr Lys Ala Leu Phe Ala Phe Glu Glu Ile Asp Gly Val Asp Val
    1395                1400                1405 tgc ttt ttt ggg atg cat gtg caa gat acg gct ctg att gcc ccc cac    4272
Cys Phe Phe Gly Met His Val Gln Asp Thr Ala Leu Ile Ala Pro His
1410                1415                1420 caa ata caa ggc tgt gta tac ata tct tat ctg gac agt att cat ttc    4320
Gln Ile Gln Gly Cys Val Tyr Ile Ser Tyr Leu Asp Ser Ile His Phe
1425                1430                1435                1440 ttc cgg ccc cgc tgc ctc cgg aca gct gtt tac cat gag atc ctc atc    4368
Phe Arg Pro Arg Cys Leu Arg Thr Ala Val Tyr His Glu Ile Leu Ile
            1445                1450                1455 gga tat ctc gag tat gtg aag aaa ttg gtg tat gtg aca gca cat att    4416
Gly Tyr Leu Glu Tyr Val Lys Lys Leu Val Tyr Val Thr Ala His Ile
        1460                1465                1470 tgg gcc tgt ccc cca agt gaa gga gat gac tat atc ttt cat tgc cac    4464
Trp Ala Cys Pro Pro Ser Glu Gly Asp Asp Tyr Ile Phe His Cys His
    1475                1480                1485 ccc cct gac cag aaa atc ccc aaa cca aaa cga cta cag gag tgg tac    4512
Pro Pro Asp Gln Lys Ile Pro Lys Pro Lys Arg Leu Gln Glu Trp Tyr
1490                1495                1500 aag aag atg ctg gac aag gcg ttt gca gag agg atc att aac gac tat    4560
Lys Lys Met Leu Asp Lys Ala Phe Ala Glu Arg Ile Ile Asn Asp Tyr
1505                1510                1515                1520 aag gac atc ttc aaa caa gcg aac gaa gac agg ctc acg agt gcc aag    4608
Lys Asp Ile Phe Lys Gln Ala Asn Glu Asp Arg Leu Thr Ser Ala Lys
            1525                1530                1535 gag ttg ccc tat ttt gaa gga gat ttc tgg cct aat gtg ttg gaa gaa    4656
```

```
Glu Leu Pro Tyr Phe Glu Gly Asp Phe Trp Pro Asn Val Leu Glu Glu
        1540                1545                1550 agc att aag gaa cta gaa caa gaa gaa gaa agg aaa aaa gaa gag           4704
Ser Ile Lys Glu Leu Glu Gln Glu Glu Glu Arg Lys Lys Glu Glu
    1555                1560                1565 agt act gca gcg agt gag act cct gag ggc agt cag ggt gac agc aaa       4752
Ser Thr Ala Ala Ser Glu Thr Pro Glu Gly Ser Gln Gly Asp Ser Lys
        1570                1575                1580 aat gcg aag aaa aag aac aac aag aag acc aac aaa aac aaa agc agc       4800
Asn Ala Lys Lys Lys Asn Asn Lys Lys Thr Asn Lys Asn Lys Ser Ser
1585                1590                1595                1600 att agc cgc gcc aac aag aag aag ccc agc atg ccc aat gtt tcc aac       4848
Ile Ser Arg Ala Asn Lys Lys Lys Pro Ser Met Pro Asn Val Ser Asn
            1605                1610                1615 gac ctg tcg cag aag ctg tat gcc acc atg gag aag cac aag gag gta       4896
Asp Leu Ser Gln Lys Leu Tyr Ala Thr Met Glu Lys His Lys Glu Val
        1620                1625                1630 ttc ttt gtg att cat ctg cat gct ggg cct gtt atc agc act cag ccc       4944
Phe Phe Val Ile His Leu His Ala Gly Pro Val Ile Ser Thr Gln Pro
            1635                1640                1645 ccc atc gtg gac cct gat cct ctg ctt agc tgt gac ctc atg gat ggg       4992
Pro Ile Val Asp Pro Asp Pro Leu Leu Ser Cys Asp Leu Met Asp Gly
        1650                1655                1660 cga gat gcc ttc ctc acc ctg gcc aga gac aag cac tgg gaa ttc tct       5040
Arg Asp Ala Phe Leu Thr Leu Ala Arg Asp Lys His Trp Glu Phe Ser
1665                1670                1675                1680 tcc tta cgc cgc tcc aaa tgg tcc act ctg tgc atg ctg gtg gag ctg       5088
Ser Leu Arg Arg Ser Lys Trp Ser Thr Leu Cys Met Leu Val Glu Leu
            1685                1690                1695 cac aca cag ggc cag gac cgc ttt gtt tat acc tgc aat gag tgc aaa       5136
His Thr Gln Gly Gln Asp Arg Phe Val Tyr Thr Cys Asn Glu Cys Lys
        1700                1705                1710 cac cat gtg gaa aca cgc tgg cac tgc act gtg tgt gag gac tat gac       5184
His His Val Glu Thr Arg Trp His Cys Thr Val Cys Glu Asp Tyr Asp
            1715                1720                1725 ctt tgt atc aat tgc tac aac aca aag agc cac acc cat aag atg gtg       5232
Leu Cys Ile Asn Cys Tyr Asn Thr Lys Ser His Thr His Lys Met Val
        1730                1735                1740 aag tgg ggg cta ggc cta gat gat gag ggc agc agt cag ggt gag cca       5280
Lys Trp Gly Leu Gly Leu Asp Asp Glu Gly Ser Ser Gln Gly Glu Pro
1745                1750                1755                1760 cag tcc aag agc ccc cag gaa tcc cgg cgt ctc agc atc cag cgc tgc       5328
Gln Ser Lys Ser Pro Gln Glu Ser Arg Arg Leu Ser Ile Gln Arg Cys
            1765                1770                1775 atc cag tcc ctg gtg cat gcc tgc cag tgt cgc aat gcc aac tgc tca       5376
Ile Gln Ser Leu Val His Ala Cys Gln Cys Arg Asn Ala Asn Cys Ser
        1780                1785                1790 ctg ccg tct tgc cag aag atg aag cga gtc gtg cag cac acc aag ggc       5424
Leu Pro Ser Cys Gln Lys Met Lys Arg Val Val Gln His Thr Lys Gly
            1795                1800                1805 tgc aag cgc aag act aat gga gga tgc cca gtg tgc aag cag ctc att       5472
Cys Lys Arg Lys Thr Asn Gly Gly Cys Pro Val Cys Lys Gln Leu Ile
        1810                1815                1820 gct ctt tgc tgt tac cac gcc aaa cac tgc caa gaa aat aaa tgc cct       5520
Ala Leu Cys Cys Tyr His Ala Lys His Cys Gln Glu Asn Lys Cys Pro
1825                1830                1835                1840 gtg ccc ttc tgc ctc aac atc aaa cat aac gtc cgc cag cag cag atc       5568
Val Pro Phe Cys Leu Asn Ile Lys His Asn Val Arg Gln Gln Gln Ile
            1845                1850                1855
```

```
cag cac tgc ctg cag cag gct cag ctc atg cgc cgg cga atg gca acc        5616
Gln His Cys Leu Gln Gln Ala Gln Leu Met Arg Arg Arg Met Ala Thr
            1860                1865                1870 atg aac acc cgc aat gtg cct cag cag agt ttg cct tct cct acc tca        5664
Met Asn Thr Arg Asn Val Pro Gln Gln Ser Leu Pro Ser Pro Thr Ser
            1875                1880                1885 gca cca ccc ggg act cct aca cag cag ccc agc aca ccc caa aca cca        5712
Ala Pro Pro Gly Thr Pro Thr Gln Gln Pro Ser Thr Pro Gln Thr Pro
            1890                1895                1900 cag ccc cca gcc cag cct cag cct tca cct gtt aac atg tca cca gca        5760
Gln Pro Pro Ala Gln Pro Gln Pro Ser Pro Val Asn Met Ser Pro Ala
1905                1910                1915                1920 ggc ttc cct aat gta gcc cgg act cag ccc cca aca ata gtg tct gct        5808
Gly Phe Pro Asn Val Ala Arg Thr Gln Pro Pro Thr Ile Val Ser Ala
            1925                1930                1935 ggg aag cct acc aac cag gtg cca gct ccc cca ccc cct gcc cag ccc        5856
Gly Lys Pro Thr Asn Gln Val Pro Ala Pro Pro Pro Ala Gln Pro
            1940                1945                1950 cca cct gca gca gta gaa gca gcc cgg caa att gaa cgt gag gcc cag        5904
Pro Pro Ala Ala Val Glu Ala Ala Arg Gln Ile Glu Arg Glu Ala Gln
            1955                1960                1965 cag cag cag cac cta tac cga gca aac atc aac aat ggc atg ccc cca        5952
Gln Gln Gln His Leu Tyr Arg Ala Asn Ile Asn Asn Gly Met Pro Pro
            1970                1975                1980 gga cgt gac ggt atg ggg acc cca gga agc caa atg act cct gtg ggc        6000
Gly Arg Asp Gly Met Gly Thr Pro Gly Ser Gln Met Thr Pro Val Gly
1985                1990                1995                2000 ctg aat gtg ccc cgt ccc aac caa gtc agt ggg cct gtc atg tct agt        6048
Leu Asn Val Pro Arg Pro Asn Gln Val Ser Gly Pro Val Met Ser Ser
            2005                2010                2015 atg cca cct ggg cag tgg cag cag gca ccc atc cct cag cag cag ccg        6096
Met Pro Pro Gly Gln Trp Gln Gln Ala Pro Ile Pro Gln Gln Gln Pro
            2020                2025                2030 atg cca ggc atg ccc agg cct gta atg tcc atg cag gcc cag gca gca        6144
Met Pro Gly Met Pro Arg Pro Val Met Ser Met Gln Ala Gln Ala Ala
            2035                2040                2045 gtg gct ggg cca cgg atg ccc aat gtg cag cca aac agg agc atc tcg        6192
Val Ala Gly Pro Arg Met Pro Asn Val Gln Pro Asn Arg Ser Ile Ser
    2050                2055                2060 cca agt gcc ctg caa gac ctg cta cgg acc cta aag tca ccc agc tct        6240
Pro Ser Ala Leu Gln Asp Leu Leu Arg Thr Leu Lys Ser Pro Ser Ser
2065                2070                2075                2080 cct cag cag cag cag cag gtg ctg aac atc ctt aaa tca aac cca cag        6288
Pro Gln Gln Gln Gln Gln Val Leu Asn Ile Leu Lys Ser Asn Pro Gln
            2085                2090                2095 cta atg gca gct ttc atc aaa cag cgc aca gcc aag tat gtg gcc aat        6336
Leu Met Ala Ala Phe Ile Lys Gln Arg Thr Ala Lys Tyr Val Ala Asn
            2100                2105                2110 cag cct ggc atg cag ccc cag ccc gga ctt caa tcc cag cct ggt atg        6384
Gln Pro Gly Met Gln Pro Gln Pro Gly Leu Gln Ser Gln Pro Gly Met
            2115                2120                2125 cag ccc cag cct ggc atg cac cag cag cct agt ttg caa aac ctg aac        6432
Gln Pro Gln Pro Gly Met His Gln Gln Pro Ser Leu Gln Asn Leu Asn
            2130                2135                2140 gca atg caa gct ggt gtg cca cgg cct ggt gtg cct cca cca caa cca        6480
Ala Met Gln Ala Gly Val Pro Arg Pro Gly Val Pro Pro Pro Gln Pro
2145                2150                2155                2160 gca atg gga ggc ctg aat ccc cag gga caa gct ctg aac atc atg aac        6528
Ala Met Gly Gly Leu Asn Pro Gln Gly Gln Ala Leu Asn Ile Met Asn
            2165                2170                2175
```

```
cca gga cac aac ccc aac atg aca aac atg aat cca cag tac cga gaa      6576
Pro Gly His Asn Pro Asn Met Thr Asn Met Asn Pro Gln Tyr Arg Glu
            2180                2185                2190 atg gtg agg aga cag ctg cta cag cac cag cag cag cag cag caa cag      6624
Met Val Arg Arg Gln Leu Leu Gln His Gln Gln Gln Gln Gln Gln Gln
        2195                2200                2205 cag cag cag cag cag caa caa caa aat agt gcc agc ttg gcc ggg ggc      6672
Gln Gln Gln Gln Gln Gln Gln Gln Asn Ser Ala Ser Leu Ala Gly Gly
    2210                2215                2220 atg gcg gga cac agc cag ttc cag cag cca caa gga cct gga ggt tat      6720
Met Ala Gly His Ser Gln Phe Gln Gln Pro Gln Gly Pro Gly Gly Tyr
2225                2230                2235                2240 gcc cca gcc atg cag cag caa cgc atg caa cag cac ctc ccc atc cag      6768
Ala Pro Ala Met Gln Gln Gln Arg Met Gln Gln His Leu Pro Ile Gln
            2245                2250                2255 ggc agc tcc atg ggc cag atg gct gct cca atg gga caa ctt ggc cag      6816
Gly Ser Ser Met Gly Gln Met Ala Ala Pro Met Gly Gln Leu Gly Gln
        2260                2265                2270 atg ggg cag cct ggg cta ggg gca gac agc acc cct aat atc cag cag      6864
Met Gly Gln Pro Gly Leu Gly Ala Asp Ser Thr Pro Asn Ile Gln Gln
    2275                2280                2285 gcc ctg cag caa cgg att ctg cag cag cag cag atg aag caa caa att      6912
Ala Leu Gln Gln Arg Ile Leu Gln Gln Gln Gln Met Lys Gln Gln Ile
2290                2295                2300 ggg tca cca ggc cag ccg aac ccc atg agc ccc cag cag cac atg ctc      6960
Gly Ser Pro Gly Gln Pro Asn Pro Met Ser Pro Gln Gln His Met Leu
2305                2310                2315                2320 tca gga cag cca cag gcc tca cat ctc cct ggc cag cag atc gcc aca      7008
Ser Gly Gln Pro Gln Ala Ser His Leu Pro Gly Gln Gln Ile Ala Thr
            2325                2330                2335 tcc ctt agt aac cag gtg cga tct cca gcc cct gtg cag tct cca cgg      7056
Ser Leu Ser Asn Gln Val Arg Ser Pro Ala Pro Val Gln Ser Pro Arg
        2340                2345                2350 ccc caa tcc caa cct cca cat tcc agc ccg tca cca cgg ata caa ccc      7104
Pro Gln Ser Gln Pro Pro His Ser Ser Pro Ser Pro Arg Ile Gln Pro
    2355                2360                2365 cag cct tca cca cac cat gtt tca ccc cag act gga acc cct cac cct      7152
Gln Pro Ser Pro His His Val Ser Pro Gln Thr Gly Thr Pro His Pro
2370                2375                2380 gga ctc gca gtc acc atg gcc agc tcc atg gat cag gga cac ctg ggg      7200
Gly Leu Ala Val Thr Met Ala Ser Ser Met Asp Gln Gly His Leu Gly
2385                2390                2395                2400 aac cct gaa cag agt gca atg ctc ccc cag ctg aat acc ccc aac agg      7248
Asn Pro Glu Gln Ser Ala Met Leu Pro Gln Leu Asn Thr Pro Asn Arg
            2405                2410                2415 agc gca ctg tcc agt gaa ctg tcc ctg gtt ggt gat acc acg gga gac      7296
Ser Ala Leu Ser Ser Glu Leu Ser Leu Val Gly Asp Thr Thr Gly Asp
        2420                2425                2430 aca cta gaa aag ttt gtg gag ggt ttg tag                              7326
Thr Leu Glu Lys Phe Val Glu Gly Leu
    2435                2440
```

<210> SEQ ID NO 2
<211> LENGTH: 2441
<212> TYPE: PRT
<213> ORGANISM: Mus
<220> FEATURE:
<221> NAME/KEY: VARIANT
<222> LOCATION: (1)...(2441)
<223> OTHER INFORMATION: Xaa = Any Amino Acid

<400> SEQUENCE: 2

| | | | | | | | | | | | | | | |
|---|---|---|---|---|---|---|---|---|---|---|---|---|---|---|
|Met|Ala|Glu|Asn|Leu|Leu|Asp|Gly|Pro|Pro|Asn|Pro|Lys|Arg|Ala|Lys|
|1| | | |5| | | | |10| | | | |15| |

Leu Ser Ser Pro Gly Phe Ser Ala Asn Asp Thr Asp Phe Gly Ser
              20                  25                30

Leu Phe Asp Leu Glu Asn Asp Leu Pro Asp Glu Leu Ile Pro Asn Gly
      35                  40                45

Glu Leu Ser Leu Leu Asn Ser Gly Asn Leu Val Pro Asp Ala Ala Ser
50                  55                60

Lys His Lys Gln Leu Ser Glu Leu Leu Arg Gly Ser Gly Ser Ser
65               70              75              80

Ile Asn Pro Gly Ile Gly Asn Val Ser Ala Ser Ser Pro Val Gln Gln
            85                90              95

Gly Leu Gly Gly Gln Ala Gln Gly Gln Pro Asn Ser Thr Asn Met Ala
         100              105            110

Ser Leu Gly Ala Met Gly Lys Ser Pro Leu Asn Gln Gly Asp Ser Ser
      115                120            125

Thr Pro Asn Leu Pro Lys Gln Ala Ala Ser Thr Ser Gly Pro Thr Pro
   130               135              140

Pro Ala Ser Gln Ala Leu Asn Pro Gln Ala Gln Lys Gln Val Gly Leu
145               150              155              160

Val Thr Ser Ser Pro Ala Thr Ser Gln Thr Gly Pro Gly Ile Cys Met
            165              170            175

Asn Ala Asn Phe Asn Gln Thr His Pro Gly Leu Leu Asn Ser Asn Ser
         180              185            190

Gly His Ser Leu Met Asn Gln Ala Gln Gln Gly Gln Ala Gln Val Met
      195              200            205

Asn Gly Ser Leu Gly Ala Ala Gly Arg Gly Arg Gly Ala Gly Met Pro
   210               215              220

Tyr Pro Ala Pro Ala Met Gln Gly Ala Thr Ser Ser Val Leu Ala Glu
225               230              235              240

Thr Leu Thr Gln Val Ser Pro Gln Met Ala Gly His Ala Gly Leu Asn
            245              250            255

Thr Ala Gln Ala Gly Gly Met Thr Lys Met Gly Met Thr Gly Thr Thr
      260              265            270

Ser Pro Phe Gly Gln Pro Phe Ser Gln Thr Gly Gly Gln Gln Met Gly
      275              280            285

Ala Thr Gly Val Asn Pro Gln Leu Ala Ser Lys Gln Ser Met Val Asn
   290               295            300

Ser Leu Pro Ala Phe Pro Thr Asp Ile Lys Asn Thr Ser Val Thr Thr
305               310              315              320

Val Pro Asn Met Ser Gln Leu Gln Thr Ser Val Gly Ile Val Pro Thr
         325              330            335

Gln Ala Ile Ala Thr Gly Pro Thr Ala Asp Pro Glu Lys Arg Lys Leu
      340              345            350

Ile Gln Gln Gln Leu Val Leu Leu Leu His Ala His Lys Cys Gln Arg
      355              360            365

Arg Glu Gln Ala Asn Gly Glu Val Xaa Ala Cys Ser Leu Pro His Cys
   370               375              380

Arg Thr Met Lys Asn Val Leu Asn His Met Thr His Cys Gln Ala Pro
385               390              395              400

Lys Ala Cys Gln Val Ala His Cys Ala Ser Ser Arg Gln Ile Ile Ser
      405              410            415

```
His Trp Lys Asn Cys Thr Arg His Asp Cys Pro Val Cys Leu Pro Leu
            420                 425                 430

Lys Asn Ala Ser Asp Lys Arg Asn Gln Gln Thr Ile Leu Gly Ser Pro
            435                 440                 445

Ala Ser Gly Ile Gln Asn Thr Ile Gly Ser Val Gly Ala Gly Gln Gln
            450                 455                 460

Asn Ala Thr Ser Leu Ser Asn Pro Asn Pro Ile Asp Pro Ser Ser Met
465                 470                 475                 480

Gln Arg Ala Tyr Ala Ala Leu Gly Leu Pro Tyr Met Asn Gln Pro Gln
                485                 490                 495

Thr Gln Leu Gln Pro Gln Val Pro Gly Gln Gln Pro Ala Gln Pro Pro
            500                 505                 510

Ala His Gln Gln Met Arg Thr Leu Asn Ala Leu Gly Asn Asn Pro Met
            515                 520                 525

Ser Val Pro Ala Gly Gly Ile Thr Thr Asp Gln Gln Pro Pro Asn Leu
            530                 535                 540

Ile Ser Glu Ser Ala Leu Pro Thr Ser Leu Gly Ala Thr Asn Pro Leu
545                 550                 555                 560

Met Asn Asp Gly Ser Asn Ser Gly Asn Ile Gly Ser Leu Ser Thr Ile
                565                 570                 575

Pro Thr Ala Ala Pro Pro Ser Ser Thr Gly Val Arg Lys Gly Trp His
                580                 585                 590

Glu His Val Thr Gln Asp Leu Arg Ser His Leu Val His Lys Leu Val
            595                 600                 605

Gln Ala Ile Phe Pro Thr Pro Asp Pro Ala Ala Leu Lys Asp Arg Arg
            610                 615                 620

Met Glu Asn Leu Val Ala Tyr Ala Lys Lys Val Glu Gly Asp Met Tyr
625                 630                 635                 640

Glu Ser Ala Asn Ser Arg Asp Glu Tyr Tyr His Leu Leu Ala Glu Lys
                645                 650                 655

Ile Tyr Lys Ile Gln Lys Glu Leu Glu Glu Lys Arg Arg Thr Arg Leu
            660                 665                 670

His Lys Gln Gly Ile Leu Gly Asn Gln Pro Ala Leu Pro Ala Ser Gly
            675                 680                 685

Ala Gln Pro Pro Val Ile Pro Pro Ala Gln Ser Val Arg Pro Pro Asn
            690                 695                 700

Gly Pro Leu Pro Leu Pro Val Asn Arg Met Gln Val Ser Gln Gly Met
705                 710                 715                 720

Asn Ser Phe Asn Pro Met Ser Leu Gly Asn Val Gln Leu Pro Gln Ala
                725                 730                 735

Pro Met Gly Pro Arg Ala Ala Ser Pro Met Asn His Ser Val Gln Met
            740                 745                 750

Asn Ser Met Ala Ser Val Pro Gly Met Ala Ile Ser Pro Ser Arg Met
            755                 760                 765

Pro Gln Pro Pro Asn Met Met Gly Thr His Ala Asn Asn Ile Met Ala
            770                 775                 780

Gln Ala Pro Thr Gln Asn Gln Phe Leu Pro Gln Asn Gln Phe Pro Ser
785                 790                 795                 800

Ser Ser Gly Ala Met Ser Val Asn Ser Val Gly Met Gly Gln Pro Ala
                805                 810                 815

Ala Gln Ala Gly Val Ser Gln Gly Gln Glu Pro Gly Ala Ala Leu Pro
            820                 825                 830
```

```
Asn Pro Leu Asn Met Leu Ala Pro Gln Ala Ser Gln Leu Pro Cys Pro
        835                 840                 845

Pro Val Thr Gln Ser Pro Leu His Pro Thr Pro Pro Ala Ser Thr
    850                 855                 860

Ala Ala Gly Met Pro Ser Leu Gln His Pro Thr Ala Pro Gly Met Thr
865                 870                 875                 880

Pro Pro Gln Pro Ala Ala Pro Thr Gln Pro Ser Thr Pro Val Ser Ser
                885                 890                 895

Gly Gln Thr Pro Thr Pro Thr Pro Gly Ser Val Pro Ser Ala Ala Gln
                900                 905                 910

Thr Gln Ser Thr Pro Thr Val Gln Ala Ala Gln Ala Gln Val Thr
        915                 920                 925

Pro Gln Pro Gln Thr Pro Val Gln Pro Pro Ser Val Ala Thr Pro Gln
    930                 935                 940

Ser Ser Gln Gln Gln Pro Thr Pro Val His Thr Gln Pro Pro Gly Thr
945                 950                 955                 960

Pro Leu Ser Gln Ala Ala Ala Ser Ile Asp Asn Arg Val Pro Thr Pro
                965                 970                 975

Ser Thr Val Thr Ser Ala Glu Thr Ser Ser Gln Gln Pro Gly Pro Asp
                980                 985                 990

Val Pro Met Leu Glu Met Lys Thr Glu Val Gln Thr Asp Asp Ala Glu
        995                 1000                1005

Pro Glu Pro Thr Glu Ser Lys Gly Glu Pro Arg Ser Glu Met Met Glu
    1010                1015                1020

Glu Asp Leu Gln Gly Ser Ser Gln Val Lys Glu Glu Thr Asp Thr Thr
1025                1030                1035                1040

Glu Gln Lys Ser Glu Pro Met Glu Val Glu Glu Lys Lys Pro Glu Val
                1045                1050                1055

Lys Val Glu Ala Lys Glu Glu Glu Asn Ser Ser Asn Asp Thr Ala
        1060                1065                1070

Ser Gln Ser Thr Ser Pro Ser Gln Pro Arg Lys Lys Ile Phe Lys Pro
        1075                1080                1085

Glu Glu Leu Arg Gln Ala Leu Met Pro Thr Leu Glu Ala Leu Tyr Arg
    1090                1095                1100

Gln Asp Pro Glu Ser Leu Pro Phe Arg Gln Pro Val Asp Pro Gln Leu
1105                1110                1115                1120

Leu Gly Ile Pro Asp Tyr Phe Asp Ile Val Lys Asn Pro Met Asp Leu
                1125                1130                1135

Ser Thr Ile Lys Arg Lys Leu Asp Thr Gly Gln Tyr Gln Glu Pro Trp
                1140                1145                1150

Gln Tyr Val Asp Asp Val Arg Leu Met Phe Asn Asn Ala Trp Leu Tyr
        1155                1160                1165

Asn Arg Lys Thr Ser Arg Val Tyr Lys Phe Cys Ser Lys Leu Ala Glu
    1170                1175                1180

Val Phe Glu Gln Glu Ile Asp Pro Val Met Gln Ser Leu Gly Tyr Cys
1185                1190                1195                1200

Cys Gly Arg Lys Tyr Glu Phe Ser Pro Gln Thr Leu Cys Cys Tyr Gly
                1205                1210                1215

Lys Gln Leu Cys Thr Ile Pro Arg Asp Ala Ala Tyr Tyr Ser Tyr Gln
                1220                1225                1230

Asn Arg Tyr His Phe Cys Gly Lys Cys Phe Thr Glu Ile Gln Gly Glu
        1235                1240                1245

Asn Val Thr Leu Gly Asp Asp Pro Ser Gln Pro Gln Thr Thr Ile Ser
```

-continued

```
          1250                1255                1260
Lys Asp Gln Phe Glu Lys Lys Lys Asn Asp Thr Leu Asp Pro Glu Pro
1265                1270                1275                1280
Phe Val Asp Cys Lys Glu Cys Gly Arg Lys Met His Gln Ile Cys Val
                1285                1290                1295
Leu His Tyr Asp Ile Ile Trp Pro Ser Gly Phe Val Cys Asp Asn Cys
            1300                1305                1310
Leu Lys Lys Thr Gly Arg Pro Arg Lys Glu Asn Lys Phe Ser Ala Lys
        1315                1320                1325
Arg Leu Gln Thr Thr Arg Leu Gly Asn His Leu Glu Asp Arg Val Asn
    1330                1335                1340
Lys Phe Leu Arg Arg Gln Asn His Pro Glu Ala Gly Glu Val Phe Val
1345                1350                1355                1360
Arg Val Val Ala Ser Ser Asp Lys Thr Val Glu Val Lys Pro Gly Met
                1365                1370                1375
Lys Ser Arg Phe Val Asp Ser Gly Glu Met Ser Glu Ser Phe Pro Tyr
            1380                1385                1390
Arg Thr Lys Ala Leu Phe Ala Phe Glu Glu Ile Asp Gly Val Asp Val
        1395                1400                1405
Cys Phe Phe Gly Met His Val Gln Asp Thr Ala Leu Ile Ala Pro His
    1410                1415                1420
Gln Ile Gln Gly Cys Val Tyr Ile Ser Tyr Leu Asp Ser Ile His Phe
1425                1430                1435                1440
Phe Arg Pro Arg Cys Leu Arg Thr Ala Val Tyr His Glu Ile Leu Ile
                1445                1450                1455
Gly Tyr Leu Glu Tyr Val Lys Lys Leu Val Tyr Val Thr Ala His Ile
            1460                1465                1470
Trp Ala Cys Pro Pro Ser Glu Gly Asp Asp Tyr Ile Phe His Cys His
        1475                1480                1485
Pro Pro Asp Gln Lys Ile Pro Lys Pro Lys Arg Leu Gln Glu Trp Tyr
    1490                1495                1500
Lys Lys Met Leu Asp Lys Ala Phe Ala Glu Arg Ile Ile Asn Asp Tyr
1505                1510                1515                1520
Lys Asp Ile Phe Lys Gln Ala Asn Glu Asp Arg Leu Thr Ser Ala Lys
                1525                1530                1535
Glu Leu Pro Tyr Phe Glu Gly Asp Phe Trp Pro Asn Val Leu Glu Glu
            1540                1545                1550
Ser Ile Lys Glu Leu Glu Gln Glu Glu Glu Arg Lys Lys Glu Glu
        1555                1560                1565
Ser Thr Ala Ala Ser Glu Thr Pro Glu Gly Ser Gln Gly Asp Ser Lys
    1570                1575                1580
Asn Ala Lys Lys Lys Asn Asn Lys Lys Thr Asn Lys Asn Lys Ser Ser
1585                1590                1595                1600
Ile Ser Arg Ala Asn Lys Lys Pro Ser Met Pro Asn Val Ser Asn
                1605                1610                1615
Asp Leu Ser Gln Lys Leu Tyr Ala Thr Met Glu Lys His Lys Glu Val
            1620                1625                1630
Phe Phe Val Ile His Leu His Ala Gly Pro Val Ile Ser Thr Gln Pro
        1635                1640                1645
Pro Ile Val Asp Pro Asp Pro Leu Leu Ser Cys Asp Leu Met Asp Gly
    1650                1655                1660
Arg Asp Ala Phe Leu Thr Leu Ala Arg Asp Lys His Trp Glu Phe Ser
1665                1670                1675                1680
```

```
Ser Leu Arg Arg Ser Lys Trp Ser Thr Leu Cys Met Leu Val Glu Leu
            1685                1690                1695

His Thr Gln Gly Gln Asp Arg Phe Val Tyr Thr Cys Asn Glu Cys Lys
            1700                1705                1710

His His Val Glu Thr Arg Trp His Cys Thr Val Cys Glu Asp Tyr Asp
            1715                1720                1725

Leu Cys Ile Asn Cys Tyr Asn Thr Lys Ser His Thr His Lys Met Val
            1730                1735                1740

Lys Trp Gly Leu Gly Leu Asp Asp Glu Gly Ser Ser Gln Gly Glu Pro
1745                1750                1755                1760

Gln Ser Lys Ser Pro Gln Glu Ser Arg Arg Leu Ser Ile Gln Arg Cys
            1765                1770                1775

Ile Gln Ser Leu Val His Ala Cys Gln Cys Arg Asn Ala Asn Cys Ser
            1780                1785                1790

Leu Pro Ser Cys Gln Lys Met Lys Arg Val Val Gln His Thr Lys Gly
            1795                1800                1805

Cys Lys Arg Lys Thr Asn Gly Gly Cys Pro Val Cys Lys Gln Leu Ile
            1810                1815                1820

Ala Leu Cys Cys Tyr His Ala Lys His Cys Gln Glu Asn Lys Cys Pro
1825                1830                1835                1840

Val Pro Phe Cys Leu Asn Ile Lys His Asn Val Arg Gln Gln Gln Ile
            1845                1850                1855

Gln His Cys Leu Gln Gln Ala Gln Leu Met Arg Arg Arg Met Ala Thr
            1860                1865                1870

Met Asn Thr Arg Asn Val Pro Gln Gln Ser Leu Pro Ser Pro Thr Ser
            1875                1880                1885

Ala Pro Pro Gly Thr Pro Thr Gln Gln Pro Ser Thr Pro Gln Thr Pro
            1890                1895                1900

Gln Pro Pro Ala Gln Pro Gln Pro Ser Pro Val Asn Met Ser Pro Ala
1905                1910                1915                1920

Gly Phe Pro Asn Val Ala Arg Thr Gln Pro Pro Thr Ile Val Ser Ala
            1925                1930                1935

Gly Lys Pro Thr Asn Gln Val Pro Ala Pro Pro Pro Ala Gln Pro
            1940                1945                1950

Pro Pro Ala Ala Val Glu Ala Ala Arg Gln Ile Glu Arg Glu Ala Gln
        1955                1960                1965

Gln Gln Gln His Leu Tyr Arg Ala Asn Ile Asn Asn Gly Met Pro Pro
            1970                1975                1980

Gly Arg Asp Gly Met Gly Thr Pro Gly Ser Gln Met Thr Pro Val Gly
1985                1990                1995                2000

Leu Asn Val Pro Arg Pro Asn Gln Val Ser Gly Pro Val Met Ser Ser
            2005                2010                2015

Met Pro Pro Gly Gln Trp Gln Gln Ala Pro Ile Pro Gln Gln Gln Pro
            2020                2025                2030

Met Pro Gly Met Pro Arg Pro Val Met Ser Met Gln Ala Gln Ala Ala
            2035                2040                2045

Val Ala Gly Pro Arg Met Pro Asn Val Gln Pro Asn Arg Ser Ile Ser
    2050                2055                2060

Pro Ser Ala Leu Gln Asp Leu Leu Arg Thr Leu Lys Ser Pro Ser Ser
2065                2070                2075                2080

Pro Gln Gln Gln Gln Val Leu Asn Ile Leu Lys Ser Asn Pro Gln
            2085                2090                2095
```

-continued

```
Leu Met Ala Ala Phe Ile Lys Gln Arg Thr Ala Lys Tyr Val Ala Asn
            2100                2105                2110

Gln Pro Gly Met Gln Pro Gln Pro Gly Leu Gln Ser Gln Pro Gly Met
        2115                2120                2125

Gln Pro Gln Pro Gly Met His Gln Gln Pro Ser Leu Gln Asn Leu Asn
    2130                2135                2140

Ala Met Gln Ala Gly Val Pro Arg Pro Gly Val Pro Pro Gln Pro
2145                2150                2155                2160

Ala Met Gly Gly Leu Asn Pro Gln Gly Gln Ala Leu Asn Ile Met Asn
            2165                2170                2175

Pro Gly His Asn Pro Asn Met Thr Asn Met Asn Pro Gln Tyr Arg Glu
        2180                2185                2190

Met Val Arg Arg Gln Leu Leu Gln His Gln Gln Gln Gln Gln Gln Gln
    2195                2200                2205

Gln Gln Gln Gln Gln Gln Gln Asn Ser Ala Ser Leu Ala Gly Gly
2210                2215                2220

Met Ala Gly His Ser Gln Phe Gln Gln Pro Gln Gly Pro Gly Gly Tyr
2225            2230                2235                2240

Ala Pro Ala Met Gln Gln Gln Arg Met Gln Gln His Leu Pro Ile Gln
                2245                2250                2255

Gly Ser Ser Met Gly Gln Met Ala Pro Met Gly Gln Leu Gly Gln
            2260                2265                2270

Met Gly Gln Pro Gly Leu Gly Ala Asp Ser Thr Pro Asn Ile Gln Gln
        2275                2280                2285

Ala Leu Gln Gln Arg Ile Leu Gln Gln Gln Met Lys Gln Gln Ile
    2290                2295                2300

Gly Ser Pro Gly Gln Pro Asn Pro Met Ser Pro Gln Gln His Met Leu
2305                2310                2315                2320

Ser Gly Gln Pro Gln Ala Ser His Leu Pro Gly Gln Gln Ile Ala Thr
            2325                2330                2335

Ser Leu Ser Asn Gln Val Arg Ser Pro Ala Pro Val Gln Ser Pro Arg
        2340                2345                2350

Pro Gln Ser Gln Pro Pro His Ser Ser Pro Ser Pro Arg Ile Gln Pro
    2355                2360                2365

Gln Pro Ser Pro His His Val Ser Pro Gln Thr Gly Thr Pro His Pro
    2370                2375                2380

Gly Leu Ala Val Thr Met Ala Ser Ser Met Asp Gln Gly His Leu Gly
2385                2390                2395                2400

Asn Pro Glu Gln Ser Ala Met Leu Pro Gln Leu Asn Thr Pro Asn Arg
            2405                2410                2415

Ser Ala Leu Ser Ser Glu Leu Ser Leu Val Gly Asp Thr Thr Gly Asp
        2420                2425                2430

Thr Leu Glu Lys Phe Val Glu Gly Leu
    2435                2440
```

<210> SEQ ID NO 3
<211> LENGTH: 15
<212> TYPE: PRT
<213> ORGANISM: Mus

<400> SEQUENCE: 3

```
Lys Val Glu Gly Asp Met Tyr Glu Ser Ala Asn Ser Arg Asp Glu
 1               5                   10                  15
```

<210> SEQ ID NO 4

```
<211> LENGTH: 17
<212> TYPE: DNA
<213> ORGANISM: Saccharomyces cerevisiae

<400> SEQUENCE: 4
cggaggactg tcctccg                                                  17
```

IDENTIFICATION OF TRANSCRIPTION FACTOR WITHIN A CAMP-RESPONSIVE TRANSCRIPTIONAL ENHANCER BINDING PROTEIN (CREB), AND USES THEREFORE

RELATED APPLICATIONS

This is a divisional application under 37 C.F.R. 1.53(b), of U.S. Ser. No. 09/515,276, filed Feb. 29, 2000, which is a divisional application of U.S. Ser. No. 08/961,739, filed Oct. 31, 1997, now issued as U.S. Pat. No. 6,063,583 on May 16, 2000, which is a continuation-in-part application of U.S. Ser. No. 08/194,468, filed Feb. 10, 1994, now issued as U.S. Pat. No. 5,750,336 on May 12, 1998 which is incorporated by reference herein in its entirety.

ACKNOWLEDGMENT

This invention was made in part with Government support under Grant No. GM 37828 provided by the National Institutes of Health. The Government may have certain rights in this invention.

FIELD OF THE INVENTION

The present invention relates to analytical methods. In a particular aspect, the present invention relates to methods for the identification of compounds which mediate the interaction between signal dependent transcription factors and co-factor protein(s) involved in the activation of transcription. In another aspect, the present invention relates to methods for the identification of new signal dependent transcription factors. In yet another aspect, the present invention relates to methods for the identification of novel co-factor protein(s) which mediate the interaction between signal dependent transcription factors and inducer molecules involved in the activation of transcription. In yet another aspect, the present invention relates to methods for treating diabetes mellitus.

BACKGROUND OF THE INVENTION

Many eukaryotic genes are regulated in an inducible, cell type-specific fashion. Genes expressed in response to heat shock, steroid/thyroid hormones, phorbol esters, cyclic adenosine monophosphate (cAMP), growth factors. and heavy metal ions are examples of this class. The activity of cells is controlled by external signals that stimulate or inhibit intracellular events. The process by which an external signal is transmitted into and within a cell to elicit an intracellular response is referred to as signal transduction. Signal transduction is generally initiated by the interaction of extracellular factors (or inducer molecules, i.e., growth factors, hormones, adhesion molecules, neurotransmitters, and other mitogens) with receptors at the cell surface. Extracellular signals are transduced to the inner face of the cell membrane, where the cytoplasmic domains of receptor molecules contact intracellular targets. The initial receptor-target interactions stimulate a cascade of additional molecular interactions involving multiple intracellular pathways that disseminate the signal throughout the cell.

Many of the proteins involved in signal transduction contain multiple domains. Some of these domains have enzymatic activity and some of these domains are capable of binding to other cellular proteins, DNA regulatory elements, calcium, nucleotides, lipid mediators, and the like.

Protein-protein interactions are involved in all stages of the intracellular signal transduction process—at the cell membrane, where the signal is initiated in the cytoplasm by receptor recruitment of other cellular proteins, in the cytoplasm where the signals are disseminated to different cellular locations, and in the nucleus where proteins involved in transcriptional control congregate to turn on or turn off gene expression.

Mitogenic signaling affects the transcriptional activation of specific sets of genes and the inactivation of others. The nuclear effectors of gene activation are transcription factors that bind to DNA as homomeric or heteromeric dimers. Phosphorylation also modulates the function of transcription factors, as well. Oncogenes, first identified as the acute transforming genes transduced by retroviruses, are a group of dominantly acting genes. Such genes, which are involved in cell division, encode growth factors and their receptors, as well as second messengers and mitogenic nuclear proteins activated by growth factors.

The binding of growth factors to their respective receptors activates a cascade of intracellular pathways that regulate phospholipid metabolism, arachidonate metabolism, protein phosphorylation, calcium mobilization and transport, and transcriptional regulation. Specific phosphorylation events mediated by protein kinases and phosphatases modulate the activity of a variety of transcription factors within the cell. These signaling events can induce changes in cell shape, mobility, and adhesiveness, or stimulate DNA synthesis. Aberrations in these signal-induced events are associated with a variety of hyperproliferative diseases ranging from cancer to psoriasis.

The ability to repress intracellular signal-induced response pathways is an important mechanism in negative control of gene expression. Selective disruption of such pathways would allow the development of therapeutic agents capable of treating a variety of disease states related to improper activation and/or expression of specific transcription factors. For example, in patients with non-insulin dependent diabetes mellitus (NIDDM), hyperglycemia develops, in part as a result of β cell failure secondary to chronic insulin resistance. This hyperglycemia appears to be exacerbated by hyperglucogonemia and increased hepatic gluconeogenesis. cAMP appears to be the major starvation state signal which triggers glucagon gene expression as well as transcription of PEPCK, the rate limiting enzyme in gluconeogenesis.

There remains, thus, a need in the art for selective disruption of intracellular signal-induced response pathways.

SUMMARY OF THE INVENTION

In accordance with the present invention, it has been discovered that CREB binding protein (CBP) cooperates with upstream activators involved in the activation of transcription by signal dependent transcription factors, such as c-Jun (responsive to phorbol ester), serum response factor, and the like. Accordingly, assays employing CBP have been developed for the identification of compounds which disrupt the ability of signal dependent transcription factors to activate transcription. In another aspect, assays employing CBP have been developed for the identification of new signal dependent transcription factors. In yet another aspect of the present invention, assays employing CBP have been developed for the identification of novel co-factor protein(s) which mediate the interaction between signal dependent transcription factors and inducer molecules involved in the activation of transcription. In still another aspect, an assay is provided to identify compounds which have the binding and/or activation properties characteristic of CREB binding protein. In still another aspect, methods employing compounds which inhibit intracellular signal-induced response pathways have been developed for the treatment of diabetes mellitus.

DETAILED DESCRIPTION OF THE INVENTION

Figure 1:
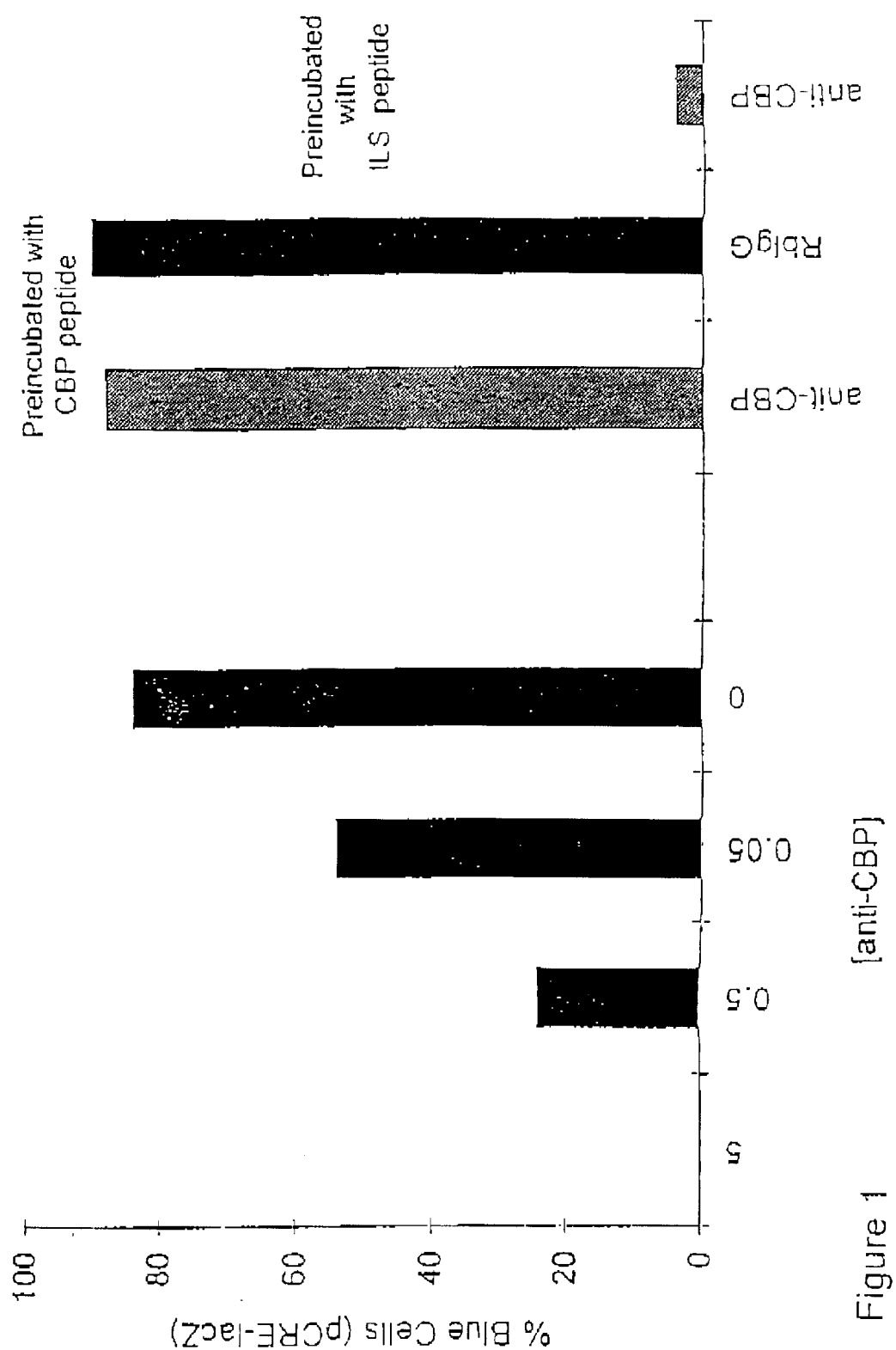
FIG. 1 is a bar graph summarizing the injections described in Example 2. Each bar represents the percentage of positive cells expressing β-galactosidase from 2–3 experiments where 100–200 cells were injected in each experiment. [anti-CBP] denotes concentration of affinity purified CBP antiserum injected into cells. Right (hatched bars) indicate the percent lacZ positive cells after microinjection of CRE-lacZ reporter with CBP antiserum (anti-CBP) or control IgG (RbIgG). Preincubation of antisera with CBP peptide or non-specific ILS peptide (1 mg/ml) was carried out as indicated.

Cyclic AMP (cAMP) regulates the transcription of numerous genes through protein kinase-A (PK-A) mediated phosphorylation, at Ser133, of transcription factor CREB. Within the CREB protein, a 60 amino acid Kinase Inducible Domain (KID) mediates transcriptional induction by PK-A. Based on recent work describing a nuclear CREB Binding Protein (CBP), it has been examined whether CBP is necessary for cAMP regulated transcription. Within CBP, a CREB binding domain has been identified, referred to as KIX which specifically interacts with the phosphorylated KID domain of CREB. About 600A of solvent accessible surface area in each protein is directly involved in formation of CREB:CBP complex. Phosphorylated Ser133 coordinates with a single arginine residue (Arg-600). The apparent Kd of the CREB:CBP complex is 0.4 μM.

Antisera against CBP have been found to completely inhibit transcription from a cAMP responsive promoter, but not from constitutively active promoters. Surprisingly, CBP has also been found to cooperate with upstream activators involved in phorbol ester and serum responsive transcription. It is demonstrated herein that recruitment of CBP to certain inducible promoters is intimately involved in transmitting inductive signals from phosphorylated, and thus activated, upstream factors to the RNA polymerase II complex. A number of analytical uses for CBP and CBP-like compounds based on these observations are described herein.

In accordance with the present invention, there is provided a method for the identification of a compound which inhibits activation of cAMP and mitogen responsive genes, said method comprising:

monitoring expression of reporter in response to exposure to said compound, relative to expression of reporter in the absence of said compound, wherein exposure to said compound is carried but in the presence of:
a signal dependent transcription factor,
a polypeptide comprising at least amino acid residues 461–661 of the protein set forth in SEQ ID NO:2, and
a reporter construct comprising a reporter gene under the control of said signal dependent transcription factor.

As employed herein, the phrase "cAMP and mitogen responsive genes" refers to early response genes which are activated in response to a diverse array of agents including mitogens, such as, growth factors, differentiation inducers and biomodulators. Examples of such agents include insulin-like growth factor (IGF-1), erythropoietin (EPO), nerve growth factor (NGF), epidermal growth factor (EGF), platelet-derived growth factor (PDGF), fibroblast growth factor (FGF), transforming growth factor β (TGFβ), interferon, tumor necrosis factor (TNF), interleukins, granulocyte-macrophage colony-stimulating factor (GM-CSF), G-CSF, prolactin, serotonin, angiotensin, bombesin, bradykinin, noradrenalin, putrescine, concanavalin A, various oncogenic agents including tumor viruses, UV irradiation, estrogen, progesterone, testosterone, glucagon, PEPCK and the like.

Signal dependent transcription factors contemplated for use in the practice of the present invention include phosphorylation dependent activators such as CREB, Jun, Fos, and other early response genes such as Myc, Myb, erbA, and Rel, serum responsive factor, Elk, as well as steroid hormone receptors (e.g., glucocorticoid receptor (GR)), and the like.

Polypeptides employed in the invention assay function as co-factors by binding to the signal dependent transcription factor as a necessary component of a transcriptionally active complex. Examples of such co-factors include CBP (i.e., substantially the entire amino acid sequence set forth in SEQ ID NO:2), a polypeptide comprising amino acid residues 1–661 as set forth in SEQ ID NO:2, as well as functional fragments thereof, e.g., residues 461–661, and homologues thereof, such as those identified by the method described herein for the identification of compounds which have the binding and/or activation properties characteristic of CREB binding protein. In accordance with one embodiment of the present invention, there are provided purified and isolated polypeptides, CBPs, that bind to a specific sequence within phosphorylated CREB.

As used herein, the term "purified" means that the molecule is substantially free of contaminants normally associated with a native or natural environment. CREB binding protein, or functional fragments thereof, useful in the practice of the present invention, can be obtained by a number of methods, e.g., precipitation, gel filtration, ion-exchange, reversed-phase, DNA affinity chromatography, and the like. Other well-known methods are described in Deutscher et al., *Guide to Protein Purification: Methods in Enzymology* Vol. 182, (Academic Press, 1990), which is incorporated herein by reference.

Alternatively, a purified CBP, or functional fragment thereof, useful in the practice of the present invention, can also be obtained by well-known recombinant methods as described, for example, in Ausubel et al., *Current Protocols in Molecular Biology* (Greene Publishing Associates, Inc. and John Wiley & Sons, Inc. 1993), also incorporated herein by reference. An example of recombinant means to prepare CBP, or functional fragments thereof, is to express nucleic acid encoding CBP, or functional fragment thereof, in a suitable host cell, such as a bacterial, yeast or mammalian cell, using methods well known in the art, and recovering the expressed protein, again using methods well known in the art.

CBPs, and biologically active fragments thereof, useful in the practice of the present invention can also be produced by chemical synthesis. Synthetic polypeptides can be produced using Applied Biosystems, Inc. Model 430A or 431A automatic polypeptide synthesizer and chemistry provided by the manufacturer. CBP, and biologically active fragments thereof, can also be isolated directly from cells which have been transformed with the expression vectors described below in more detail.

The present invention also encompasses nucleic acids encoding CBP and functional fragments thereof. See, for example, SEQ ID NO:1. This invention also encompasses nucleic acids which encode substantially the entire amino acid sequence set forth in SEQ ID NO:2 (for example, the nucleic acid sequence set forth in SEQ ID NO:1, as well as nucleic acid sequences which differ from that set forth in SEQ ID NO:1 due to the degeneracy of the genetic code), nucleic acids which encode amino acid residues 1–661, as set forth in SEQ ID NO:2, nucleic acids which encode amino acid residues 461–661, as set forth in SEQ ID NO:2, as well as nucleic acids which encode substantially the same amino acid sequences as any of those referred to above, but which differ only by the presence of conservative amino acid changes that do not alter the binding and/or activation properties of the CBP or CBP-like polypeptide encoded thereby.

The invention further provides the above-described nucleic acids operatively linked to a promoter, as well as other regulatory sequences. As used herein, the term "operatively linked" means positioned in such a manner that the promoter will direct the transcription of RNA from the nucleic acid. Examples of such promoters are SP6, T4 and T7.

Vectors which contain both a promoter and a cloning site into which a piece of DNA can be inserted so as to be operatively linked to the promoter are well known in the art. Preferably, these vectors are capable of transcribing RNA in vitro or in vivo. Examples of such vectors are the pGEM series (Promega Biotech, Madison, Wis.) This invention also provides a vector comprising a nucleic acid molecule such as DNA, cDNA or RNA encoding a CBP polypeptide. Examples of additional vectors useful herein are viruses, such as bacteriophages, baculoviruses and retroviruses, cosmids, plasmids, and the like. Nucleic acids are inserted into vector genomes by methods well known in the art. For example, insert and vector DNA can both be exposed to a restriction enzyme to create complementary ends on both molecules that base pair with each other and which are then joined together with a ligase. Alternatively, synthetic nucleic acid linkers that correspond to a restriction site in the vector DNA can be ligated to the insert DNA which is then digested with a restriction enzyme that recognizes a particular nucleotide sequence. Additionally, an oligonucleotide containing a termination codon and an appropriate restriction site can be ligated for insertion into a vector containing, for example, some or all of the following: a selectable marker gene, such as neomycin gene for selection of stable or transient transfectants in mammalian cells; enhancer/promoter sequences from the immediate early gene of human CMV for high levels of transcription; transcription termination and RNA processing signals from SV40 for mRNA stability; SV40 polyoma origins of replication and ColE1 for proper episomal replication; versatile multiple cloning sites; and T7 and SP6 RNA promoters for in vitro transcription of sense and antisense RNA: Other means are available and can readily be accessed by those of skill in the art.

Also provided are expression vectors comprising DNA encoding a mammalian CBP, or functional fragment thereof, adapted for expression in a bacterial cell, a yeast cell, a mammalian cell or other animal cell. Such vectors comprise the regulatory elements necessary for expression of the DNA in the bacterial, yeast, mammalian or animal cells. Regulatory elements are positioned relative to the DNA encoding the CBP polypeptide so as to permit expression thereof. Regulatory elements required for expression include promoter sequences to bind RNA polymerase and transcription initiation sequences for ribosome binding. For example, a bacterial expression vector includes a promoter such as the lac promoter and the Shine-Dalgarno sequence and the start codon AUG (Ausubel et al., supra 1993) for transcription initiation. Similarly a eukaryotic expression vector includes a heterologous or homologous promoter for RNA polymerase II, a downstream polyadenylation signal, the start codon AUG, and a termination codon for detachment of the ribosome. Such vectors can readily be obtained commercially or assembled by methods well known in the art, for example, the methods described above for constructing vectors in general. Expression vectors are useful to produce cells that express CBP or functional fragments thereof.

As employed herein, the term "reporter construct" refers to a recombinant construct, for example, an expression vector comprising a reporter gene under the control of a signal dependent transcription factor. In yet another example, the term refers to an expression vector comprising a reporter gene under the control of GAL4 response element. A compound which induces activation or inactivation of a target gene induces the reporter gene to express an exogenous identifiable "signal". Expression of the reporter gene indicates that the target gene has been modulated. Exemplary reporter genes encode luciferase, β-galactosidase, chloramphenicol transferase, and the like.

In practicing the assays of the present invention, reporter plasmid is introduced into suitable host cells, along with CBP or a CBP-like polypeptide (or a DNA construct encoding same) and signal dependent transcription factor. The transfected host cells are then cultured in the presence and absence (as a control) of test compound suspected of being capable of inhibiting activation of cAMP and mitogen responsive genes. Next the transfected and cultured host cells are monitored for induction (i.e., the presence) of the product of the reporter gene.

In accordance with the present invention, expression of the reporter gene can be monitored in a variety of ways. Immunological procedures useful for in vitro detection of a polypeptide in a sample include immunoassays that employ a detectable antibody. Such immunoassays include, for example, ELISA, Pandex microfluorimetric assay, agglutination assays, flow cytometry, serum diagnostic assays and immunohistochemical staining procedures which are well known in the art. An antibody can be made detectable by various means well known in the art. For example, a detectable marker can be directly or indirectly attached to the antibody. Useful markers include, for example, radionuclides, enzymes, fluorogens, chromogens and chemiluminescent labels.

In accordance with still another embodiment of the present invention, there are provided methods to identify compounds which inhibit activation of cAMP and mitogen responsive genes, preferably compounds which disrupt complex comprising CREB and CBP, said method comprising:

(a) contacting a modified host cell with a test compound, wherein said modified host cell comprises:

a first fusion protein comprising a GAL4 DNA binding domain, operatively associated with the KID domain of CREB, a second fusion protein comprising an activation domain, operatively associated with the KIX domain of CBP, and a reporter construct comprising a GAL4 response element operatively linked to a reporter gene; and (b) selecting those test compounds which cause reduced expression of the reporter gene product.

In a preferred embodiment of the present invention, the first fusion protein comprises a GAL4 DNA binding domain, operatively associated with CREB and/or the second fusion protein comprises an activation domain operatively associated with CBP.

As used herein, the term "disrupt" embraces compounds which cause substantially complete dissociation of the various components of the complex, as well as compounds which merely alter the conformation of one or more components of the complex so as to reduce the repression otherwise caused thereby.

Any cell line can be used as a suitable "host" for the functional bioassay contemplated for use in the practice of the present invention. Thus, cells contemplated for use in the practice of the present invention include transformed cells, non-transformed cells, neoplastic cells, primary cultures of different cell types, and the like. Exemplary cells which can be employed in the practice of the present invention include Schneider cells, CV-1 cells, HuTu80 cells, F9 cells, NTERA2 cells, NB4 cells, HL-60 cells, 293 cells, Hela cells, yeast cells, NIH3T3 cells and the like. Preferred host cells for use in the functional bioassay system are COS cells and CV-1 cells. COS-1 (referred to as COS) cells are monkey kidney cells that express SV40 T antigen (Tag); while CV-1 cells do not express SV40 Tag. The presence of Tag in the COS-1 derivative lines allows the introduced expression plasmid to replicate and provides a relative increase in the amount of receptor produced during the assay period. CV-1 cells are presently preferred because they are particularly convenient for gene transfer studies and provide a sensitive and well-described host cell system.

The above-described cells (or fractions thereof) are maintained under physiological conditions when contacted with physiologically active compound. "Physiological conditions" are readily understood by those of skill in the art to comprise an isotonic, aqueous nutrient medium at a temperature of about 37° C.

Various constructs employed in the practice of the present invention are well known in the art. Thus, the GAL4 DNA binding domain, the activation domain and GAL4 response elements have all been well characterized and extensively discussed in the art. For example, the DNA binding domain of the yeast GAL4 protein comprises at least the first 74 amino acids thereof (see, for example, Keegan et al., *Science* 231:699–704 (1986)). Preferably, the first 90 or more amino acids of the GAL4 protein will be used, with the first 147 amino acid residues of yeast GAL4 being presently most preferred.

Activation domains contemplated for use in the practice of the present invention are well known in the art and can readily be identified by the artisan. Examples include the GAL4 activation domain, BP64, VP16, and the like.

Exemplary GAL4 response elements are those containing the palindromic 17-mer:

5'-CGGAGGACTGTCCTCCG-3' (SEQ ID NO:4), such as, for example, 17MX, as described by Webster et al., in Cell 52:169–178 (1988), as well as derivatives thereof. Additional examples of suitable response elements include those described by Hollenberg and Evans in *Cell* 51:899–906 (1988); or Webster et al. in *Cell* 54:199–207 (1988).

As used herein, the phrase "operatively associated with" means that the respective DNA sequences (represented, for example, by the terms "GAL4 response element" and "reporter gene") are operational, i.e., work for their intended purposes; the word "functionally" means that after the two segments are linked, upon appropriate activation by a ligand-receptor complex, the reporter gene will be expressed as the result of the fact that the corresponding "response element" was "turned on" or otherwise activated.

As readily recognized by those of skill in the art, the above-described assay can be modified to facilitate identification of compounds which inhibit any of the specific interactions involved in the formation of the CREB:CBP complex.

Compounds which are capable of inhibiting activation of cAMP and mitogen responsive genes, and hence can be identified by the invention assay method, include antibodies raised against the binding domain of the protein set forth in SEQ ID NO:2, antibodies raised against the binding domain of CBP-like compounds, and the like. Presently preferred antibodies are those raised against a polypeptide fragment comprising amino acid residues from about 461 up to 661 of the protein set forth in SEQ ID NO:2; with antibodies raised against a polypeptide fragment comprising amino acid residues from about 634 up to 648 of the protein set forth in SEQ ID NO:2 (this subfragment is also set forth specifically as SEQ ID NO:3), being especially preferred. Alternatively, antibodies which are raised against the amino acid residues surrounding residue 600 of CBP (see SEQ ID NO:2) or antibodies which inhibit the phosphorylation of residue 133 of CREB are also desired (see, for example, Parker et al., Mol Cell Biol (1996) 16(2):694–703).

Antibodies contemplated for use in the practice of the present invention have specific reactivity with the above-described CBP or CBP-like compounds. Active antibody fragments are encompassed within the definition of "antibody." As used herein "specific reactivity" refers to the ability of an antibody to recognize and bind to an epitope on CBP or CBP-like compounds. Antibodies employed in the practice of the present invention can be produced by any method known in the art. For example, polyclonal and monoclonal antibodies can be produced by methods well known in the art, as described, for example, in Harlow and Lane, *Antibodies: A Laboratory Manual* (Cold Spring Harbor Laboratory 1988), which is incorporated herein by reference. The above-described CBP or CBP-like compounds can be used as the immunogen in generating such antibodies. Altered antibodies, such as chimeric, humanized, CDR-grafted or bifunctional antibodies can also be produced by methods well known to those skilled in the art. Such antibodies can also be produced by hybridoma, chemical or recombinant methodology described, for example in Ausubel et al., supra. The antibodies can be used for determining the presence of a CBP-derived polypeptide, for the purification of CBP-derived polypeptides, for in vitro diagnostic methods, and the like.

Alternative compounds which are capable of inhibiting activation of cAMP and mitogen responsive genes include polypeptide fragments comprising amino acid residues from about 461 up to 661 of the protein set forth in SEQ ID NO:2. Polypeptide fragments comprising amino acid residues set forth specifically as SEQ ID NO:3 or KIX polypeptide fragments having a mutation at residue 600 (Arg-600), set forth in SEQ ID NO:2, are preferred, while KIX polypeptide fragments substituting Gln for Arg-600 are presently most preferred. Other polypeptide fragments contemplated for use in the practice of the present invention include those comprising the KID domain, preferably those comprising residue 133 of CREB. In the most preferred CREB polypeptide fragment, serine residue 133 is mutated to an amino acid residue which can not be phosphorylated. Other compounds which inhibit CREB activity (i.e., phosphorylated-Ser133) by binding to CBP include adenovirus E1A oncoprotein (Nakajima et al. Genes Dev (1997) 11(6):738–747), and the like. Those of skill in the art will readily recognize other polypeptide fragments which will readily inhibit the formation of CREB:CBP complex employing such assays as those disclosed herein.

In accordance with another embodiment of the present invention, there is provided a method for the identification of a compound which inhibits activation of cAMP and mitogen responsive genes, said method comprising:

(1) contacting a test system with said compound under physiological conditions; and (2) monitoring expression of reporter in response to said compound, relative to expression of reporter in the absence of said compound, wherein said reporter is encoded by a reporter construct comprising a reporter gene under the control of a signal dependent transcription factor, and wherein said test system comprises:
    said signal dependent transcription factor,
    a polypeptide comprising at least amino acid residues 461–661 of the protein set forth in SEQ ID NO:2, and
    said reporter construct.

In accordance with yet another embodiment of the present invention, there is provided a method for the identification of a compound which promotes activation of cAMP and mitogen responsive genes, said method comprising:

monitoring expression of reporter in response to exposure to said compound, relative to expression of reporter in the absence of said compound,
    wherein exposure to said compound is carried out in the presence of:
        a signal dependent transcription factor, or
        a polypeptide comprising at least amino acid residues 461–661 of the protein set forth in SEQ ID NO:2, and
        a reporter construct;
    wherein said reporter construct comprises a reporter gene under the control of a signal dependent transcription factor.

In accordance with still another embodiment of the present invention, there is provided a method for the identification of a compound which has the binding and/or activation properties characteristic of CREB binding protein, said method comprising:

monitoring expression of reporter in response to exposure to said compound, relative to expression of reporter in the absence of said compound,
    wherein exposure to said compound is carried out in the presence of:
        a signal dependent transcription factor, and
        a reporter construct,
    wherein said reporter construct comprises a reporter gene under the control of a signal dependent transcription factor.

In accordance with a still further embodiment of the present invention, there is provided methods for the identification of a compound which has the transcription activation properties characteristic of a signal dependent transcription factor, said method comprising:

monitoring expression of reporter in response to exposure to said compound, relative to expression of reporter in the absence of said compound,
    wherein exposure to said compound is carried out in the presence of:
        a polypeptide comprising at least amino acid residues 461–661 of the protein set forth in SEQ ID NO:2, and
        a reporter construct,
    wherein said reporter construct comprises a reporter gene under the control of a signal dependent transcription factor.

In accordance with a still further embodiment of the present invention, there are provided methods for treating diabetes mellitus, said method comprising contacting a biological system with an amount of an effective amount of a compound which inhibits binding of CREB to CBP. Such methods ameliorate hyperglycemia associated with diabetes mellitus by modulating gluconeogenesis and/or hyperglucagonemia. Particularly, such methods employ compounds which disrupt the formation of CREB:CBP complexes, thus inhibiting transcription of PEPCK or glucogon gene.

As employed herein, the phrase "biological system" refers to an intact organism or a cell-based system containing the various components required for response to the ligands described herein, e.g., an isoform of RAR (i.e., RARα, RARβ or RARγ), a silent partner for the RAR isoform (e.g., RXR), and an RAR-responsive reporter (which typically comprises an RAR response element (RARE) in operative communication with a reporter gene; suitable reporters include luciferase, chloramphenicol transferase, β-galactosidase, and the like.

Contacting in a biological system contemplated by the present invention can be accomplished in a variety of ways, and the treating agents contemplated for use herein can be administered in a variety of forms (e.g., in combination with a pharmaceutically acceptable carrier therefor) and by a variety of modes of delivery. Exemplary pharmaceutically acceptable carriers include carriers suitable for oral, intravenous, subcutaneous, intramuscular, intracutaneous, and the like administration. Administration in the form of creams, lotions, tablets, dispersible powders, granules, syrups, elixirs, sterile aqueous or non-aqueous solutions, suspensions or emulsions, and the like, is contemplated.

For the preparation of oral liquids, suitable carriers include emulsions, solutions, suspensions, syrups, and the like, optionally containing additives such as wetting agents, emulsifying and suspending agents, sweetening, flavoring and perfuming agents, and the like.

For the preparation of fluids for parenteral administration, suitable carriers include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized, for example, by filtration through a bacteria-retaining filter, by incorporating sterilizing agents into the compositions, by irradiating the compositions, or by heating the compositions. They can also be manufactured in the form of sterile water, or some other sterile injectable medium immediately before use.

As employed herein, the phrase "effective amount" refers to levels of compound sufficient to provide circulating concentrations high enough to modulate the expression of gene(s) mediated by members of the steroid/thyroid superfamily of receptors. Such a concentration typically falls in the range of about 10 nM up to 2 $\mu$M; with concentrations in the range of about 100 nM up to 500 nM being preferred. Since the activity of different compounds described herein may vary considerably, and since individual subjects may present a wide variation in severity of symptoms, it is up to the practitioner to determine a subject's response to treatment and vary the dosages accordingly.

The invention will now be described in greater detail by reference to the following non-limiting examples.

EXAMPLE I

Functional Properties of CBP

To characterize the functional properties of CBP, rabbit CBP antiserum was developed against a fragment of CBP extending from amino acid residues 634–648 within the CREB binding domain of CBP (i.e., KVEGDMYESAN-SRDE; SEQ ID NO:3). Crude antiserum was affinity purified on a synthetic CBP peptide column, as described by Gonzalez et al., in *Mol. and Cell Biol.* 11(3):1306–1312 (1991), which is incorporated herein by reference. Far-Western and Western blot assays were performed as described by, for example, Chrivia et al., in *Nature* 365:855–859 (1993), also incorporated herein by reference. Thus, Western (CBP) and Far-Western ($^{32}$P-CREB) blot analysis of partially purified CBP protein from HeLa nuclear extract was carried out following SDS-PAGE and transfer to nitrocellulose. Far-Western blots were also obtained for crude HeLa nuclear extracts using $^{32}$P-labeled CREB, phosphorylated with PK-A or casein kinase II (CKII). Far-Western blot analysis was also conducted with immunoprecipitates prepared from HeLa nuclear extracts with control IgG or affinity purified CBP antiserum (CBP-Ab). CREB binding activity was detected with $^{32}$P-labeled CREB phosphorylated with PK-A.

Using the above-described antiserum, a 265 kD polypeptide was detected on Western blots, as predicted from the cDNA (see Chrivia et al., supra), which coincided with the predominant phospho-CREB binding activity in HeLa nuclear extracts by "Far-Western" blot assay. An identical phospho-CREB binding activity was also found in NIH3T3 cells. This phospho-CREB binding protein appeared to be specific for Ser133 phosphorylated CREB because no such band was detected with CREB labeled to the same specific activity at a non-regulatory phospho-acceptor site (Ser156) by casein kinase II (CKII) (see Hagiwara et al., *Cell* 70:105–113 (1992), which is incorporated herein by reference).

To further demonstrate that the major phospho-CREB binding protein in HeLa and NIH3T3 cells is specifically bound by the anti-CBP antibody, immunoprecipitates were prepared from crude nuclear extracts using the CBP antiserum. Far-Western analysis of these immunoprecipitates revealed a 265 kD band in samples incubated with CBP antiserum, but not with control IgG.

EXAMPLE II

Role of Phosphorylation in CREB-CBP Interaction

To examine whether the phosphorylation dependent interaction between CREB and CBP was critical for cAMP responsive transcription, a microinjection assay was employed using CBP antiserum, which would be predicted to impair formation of a CREB-CBP complex. Thus, NIH3T3 cells were cultured in 5% $CO_2$ atmosphere in Dulbecco's Modified Eagle's Medium (DMEM), supplemented with 10% fetal calf serum. Forty-eight hours prior to injection, cells were passaged into scored glass coverslips and made quiescent by incubation in medium containing 0.05% fetal calf serum for 24 hours (see, for example, Hagikara et al., supra and Alberts et al., in *Mol. and Cell Biol.* 13:2104–2112 (1993), both incorporated herein by reference). Representative fields of NIH3T3 cells were injected with pCRE-lacZ reporter plasmid plus 5, 0.5, and 0.05 mg/ml of affinity purified CBP antiserum. Total antibody concentration in microinjected cells was maintained at 5 mg/ml by adjusting with control Rabbit IgG. Injected cells were stimulated with 0.5 mM 8-bromo-cAMP, plus 3-isobutyl-1-methylxanthine (IBMX) for 4 hours, then fixed and assayed for lacZ activity ($\beta$-Gal) as well as antibody content (Texas Red anti-Rb).

Following microinjection into nuclei of NIH3T3 cells, a CRE-lacZ reporter was markedly induced by treatment with 8-bromo-cAMP plus IBMX. Co-injection of CBP antiserum with the CRE-lacZ plasmid inhibited cAMP dependent activity in a dosage-dependent manner, but control IgG had no effect on this response.

To determine whether CBP antiserum inhibited cAMP responsive transcription by binding specifically to CBP, peptide blocking experiments were performed. Thus, the effect of CBP antiserum on CRE-lacZ reporter activity following pre-treatment of CBP antiserum with synthetic CBP peptide (anti-CBP+CBP) or unrelated peptide (anti-CBP+ILS; the unrelated peptide, ILS, is described by Leonard et al., in Mol. Endocr. 7: 1275–1283 (1993), which is incorporated herein by reference) was determined. Rabbit IgG+CBP and rabbit IgG pre-treated with CBP peptide were used as controls. NIH3T3 cells were injected with CRE-lacZ reporter plus various CBP antisera, stimulated with 0.5 mM 8-bromo-cAMP, plus IBMX for 4 hours, and assayed for lacZ activity. Cells expressing the lacZ gene product form a blue precipitate upon X-gal staining, which quenches immunofluorescent detection of the injected antibody.

CBP antiserum, pre-incubated with synthetic CBP peptide, was unable to recognize the 265 kD CBP product on a Western blot, and could not inhibit CRE-lacZ reporter activity upon microinjection into NIH3T3 cells. But antiserum treated with an unrelated synthetic peptide (ILS) retained full activity in both Western and microinjection assay, suggesting that the ability of the antiserum to bind CBP was critical for its inhibitory effect on cAMP dependent transcription.

Results of these experiments are summarized in FIG. 1.

EXAMPLE III

Multiple Signaling Pathways Utilize CBP

To determine whether CBP activity may be restricted to a subset of promoters, several constitutively active reporter constructs were tested:

Cytomegalovirus (CMV-lacZ),

Rous sarcoma virus (RSV-lacZ), and

SV40 (SV40-lacZ)

Figure 2:
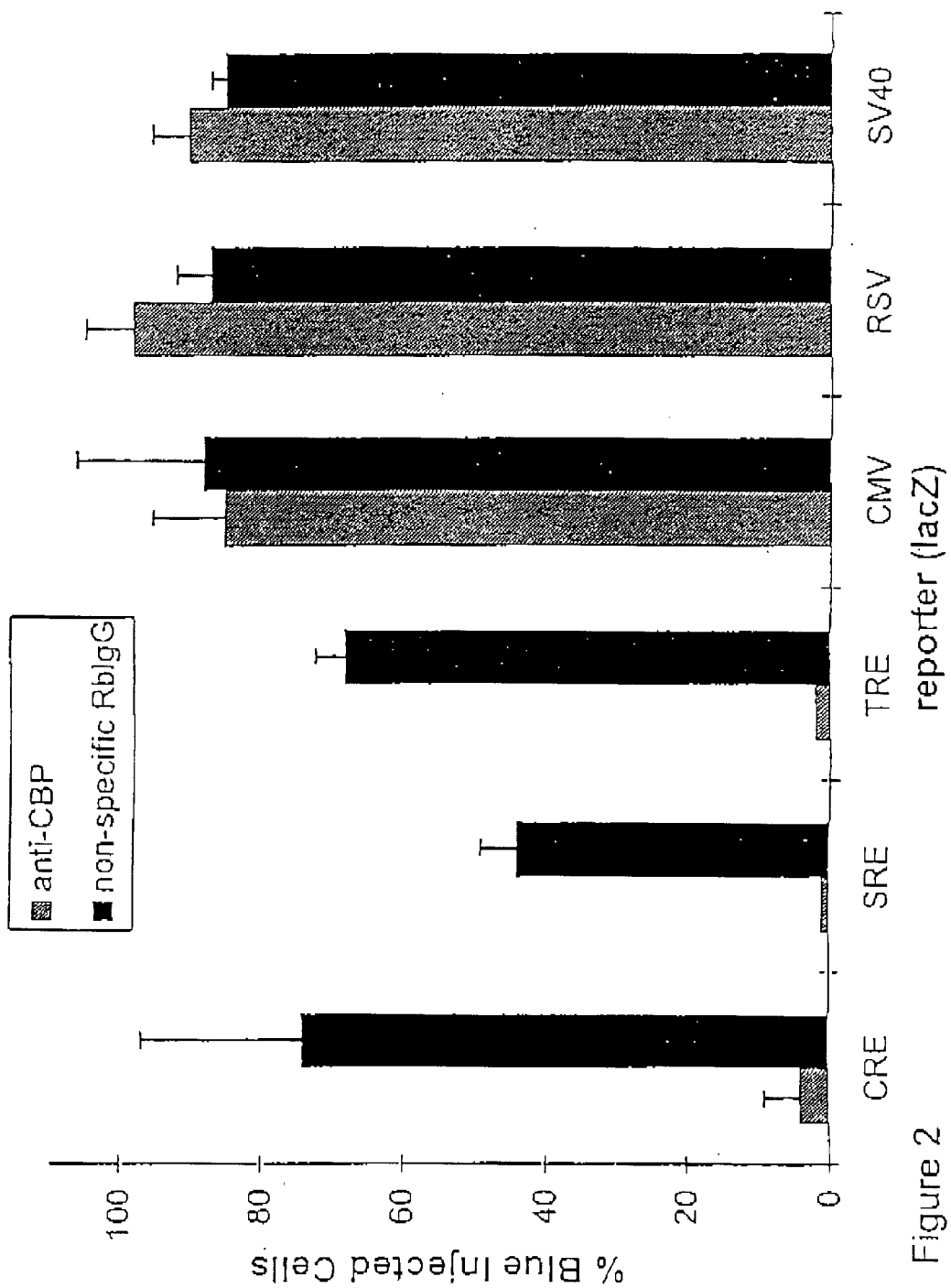
FIG. 2 is a bar graph summarizing the results of CBP antisera injections, as described in Example 3. Bars represent the percentage of lacZ positive (blue) cells (mean±standard deviation) from 3–5 experiments where 100–200 cells were injected in each experiment. Injected cells were identified by immunofluorescence and/or lacZ staining. Reporter plasmid encoding the lacZ reporter was microinjected into NIH3T3 cells. CRE-, SRE-, TRE-lacZ reporter activities were determined after microinjected cells were treated as described herein. CMV-, RSV-, and SV40-lacZ reporter activities were measured in the absence of inducers. Hatched bars indicate % blue cells after microinjection with CBP antiserum. Solid bars indicate % blue cells following injection with control rabbit IgG (RbIgG).

Thus, cells were microinjected with CBP antiserum plus Rous Sarcoma Virus (pRSV-lacZ) or Cytomegalovirus (pCMV-lacZ) reporter constructs. Alternatively, NIH3T3 cells microinjected with CBP antiserum (or non-specific rabbit IgG (RbIgG)), plus reporter constructs containing either cAMP responsive elements (pCRE-lacZ), serum responsive elements (pSRE-lacZ) or phorbol ester responsive elements (pTRE-lacZ). Light field photo-micrographs show cells stained for β-galactosidase activity following four hour treatment with either 0.5 mM 8-bromo-cAMP, plus IBMX (pCRE-lacZ), 20% fetal calf serum (pSRE-lacZ), or 200 ng/ml TPA (pTRE-lacZ). Results of β-galactosidase assays are summarized in FIG. 2. Dark field photos show microinjected IgGs as visualized by immunofluorescence using Texas Red donkey anti-rabbit IgG.

When examined in NIH3T3 cells by transient transfection assay, each of the constitutively active reporter constructs had comparable basal activity, relative to the cAMP-stimulated CRE reporter plasmid, thereby permitting the effects of CBP antiserum on these reporters to be compared directly. Although co-injected CBP antiserum could block cAMP stimulated activity from a CRE-lacZ reporter in contemporaneous assays, no inhibition was observed on basal expression from any of the constitutive promoter constructs tested, even when 10-fold lower amounts of reporter plasmid were employed.

These results suggest that CBP can indeed discriminate between basal and signal dependent activities in vivo.

EXAMPLE IV

CBP-involvement in Non-CREB Mediated Pathways

Previous reports showing that serum and phorbol esters stimulate their target genes through phosphorylation-dependent trans-activators (see, for example, Hill et al., in *Cell* 73:395–406 (1993) or Smeal et al., in *Nature* 354:494–496 (1991), both incorporated herein by reference), suggested that CBP might also function in these signaling pathways. Thus, Far-Western analyses were carried out with crude HeLa nuclear extracts using $_{32}$P-labeled recombinant Jun protein phosphorylated in vitro with either Jun-kinase (JNK; see Hibi et al., in *Genes and Develop.* 7:2135–2148 (1993), incorporated herein by reference) or casein kinase II (CK II).

Whereas serum and TPA could stimulate reporter activity in NIH3T3 cells microinjected with serum responsive element (SRE)-lacZ and TPA-responsive element (TRE)-lacZ indicator plasmids, respectively, co-injected CBP antiserum completely blocked both responses. These results suggest that CBP not only interacts with CREB, but also with other signal-dependent transcription factors.

In this regard, phorbol esters and serum induce TRE-dependent transcription, in part, through the Jun-kinase (JNK) mediated phosphorylation of c-Jun at Ser63 and Ser73 (see, for example, Smeal et al., supra or Hibi et al., supra). Using $^{32}$P-labeled recombinant c-Jun protein, phosphorylated at Ser63 and Ser73 with JNK, Far-Western blot assays were performed on crude HeLa nuclear extracts. JNK-phosphorylated c-Jun protein could bind CBP with comparable affinity to CREB. But c-Jun labeled to similar specific activity at non-activating sites (Thr 231, Ser243, and Ser249; see Boyle et al., in *Cell* 64:573–584 (1991)) by CKII, could not interact with CBP, suggesting that interaction between CBP and c-Jun requires phosphorylation of the transcriptionally active Ser63 and Ser73 phospho-acceptor sites. In view of the inhibitory effect of CBP antiserum on TRE-β gal reporter expression following phorbol ester and serum induction, the phosphorylation dependent interaction between CBP and c-Jun would appear to be a critical component of these response pathways.

EXAMPLE V

Chromatographic Purification of CBP

Based on the surprising discovery that CBP cooperates with phosphorylation dependent activators by recruiting general transcription factors to target promoters, it was next examined whether CBP would co-fractionate with any general factors in HeLa nuclear extracts. Thus, Far-Western analyses of protein fractions were obtained after phospho-cellulose chromatography. Phospho-CREB binding proteins were visualized using $^{32}$P-labeled CREB phosphorylated in vitro with PK-A ($^{32}$P-CREB). Western analysis was carried out with the same blot as described above, using affinity purified CBP antibody (CBP Ab). Far-Western ($^{32}$P-CREB) and Western (CBP-Ab) analyses of fractions were also carried out following DEAE and DE52 chromatography. Phosphocellulose, DEAE, and DE52 chromatography was performed on HeLa nuclear extracts as described by Ferreri et al., in *Proc. Natl. Acad. Sci. USA* in press (1993), which is incorporated herein by reference.

Both CBP-immunoreactive and phospho-CREB binding activities were retained on phosphocellulose columns and were eluted at 0.3–0.5M KCl. Further purification of a comparable phospho-cellulose fraction on DEAE-sepharose and DE52 resins showed that CBP was highly enriched in fractions containing TFII (E, F, H) but not TFIID activities. Although the general factor which associates directly with CBP is not known, the co-fractionation of CBP with proteins involved in basal transcription initiation suggests a testable mechanism for CBP action. In particular, the results presented herein suggest that phosphorylation-dependent activators like CREB and Jun influence assembly of late-acting factors (TFII E, F, H) during transcriptional initiation/reinitiation by interacting with CBP in a signal dependent manner.

While the invention has been described in detail with reference to certain preferred embodiments thereof, it will be understood that modifications and variations are within the spirit and scope of that which is described and claimed.

That which is claimed is:

1. An isolated nucleic acid encoding a 60 amino acid segment of a cAMP-responsive transcriptional enhancer binding protein (CREB), wherein said 60 amino acid segment is a kinase inducible domain (KID) that mediates transcriptional induction by protein kinase A (PK-A).

2. The isolated nucleic acid of claim 1, wherein KID is further characterized as specifically interacting with a CREB binding domain (KIX) of a CREB binding protein (CBP).

3. The isolated nucleic acid of claim 2, wherein KID is further characterized by having a serine residue capable of phosphorylation.

* * * * *

UNITED STATES PATENT AND TRADEMARK OFFICE
CERTIFICATE OF CORRECTION

PATENT NO. : 6,646,115 B1
DATED : November 11, 2003
INVENTOR(S) : Marc R. Montminy It is certified that error appears in the above-identified patent and that said Letters Patent is hereby corrected as shown below:

Title page,
Item [60], Related U.S. Application Data, change "continuation-in-part of application No. 08/961,739" to -- divisional of application No. 08/961,739 --

Signed and Sealed this

Thirtieth Day of March, 2004

JON W. DUDAS
*Acting Director of the United States Patent and Trademark Office*